US007803984B2

(12) United States Patent
Trick et al.

(10) Patent No.: US 7,803,984 B2
(45) Date of Patent: Sep. 28, 2010

(54) COMPOSITIONS AND METHODS FOR CONTROLLING PLANT PARASITIC NEMATODES

(75) Inventors: Harold N. Trick, Olsburg, KS (US); Judith L. Roe, Manhattan, KS (US); Timothy C. Todd, Manhattan, KS (US); Michael A. Herman, Manhattan, KS (US)

(73) Assignee: Kansas State University Research Foundation, Manhattan, KS (US)

( * ) Notice: Subject to any disclaimer, the term of this patent is extended or adjusted under 35 U.S.C. 154(b) by 572 days.

(21) Appl. No.: 10/616,390

(22) Filed: Jul. 9, 2003

(65) Prior Publication Data

US 2004/0098761 A1 May 20, 2004

Related U.S. Application Data

(60) Provisional application No. 60/395,153, filed on Jul. 10, 2002.

(51) Int. Cl.
*A01H 5/00* (2006.01)
*C12N 15/82* (2006.01)
*C12N 15/31* (2006.01)

(52) U.S. Cl. .................. 800/279; 800/298; 800/278; 800/312; 800/288; 800/287; 800/295; 435/320.1; 435/468

(58) Field of Classification Search ................. 800/288, 800/278, 279, 298, 295; 435/468, 320.1
See application file for complete search history.

(56) References Cited

U.S. PATENT DOCUMENTS

| 4,940,838 A | 7/1990 | Schilperoort et al. |
| 5,824,877 A | 10/1998 | Hinchee et al. |
| 5,981,804 A | 11/1999 | Kurimoto et al. |
| 5,981,839 A | 11/1999 | Knauf et al. |
| 6,051,757 A | 4/2000 | Barton et al. |
| 6,506,559 B1 | 1/2003 | Fire et al. |
| 2004/0133943 A1 | 7/2004 | Plaetinck et al. |
| 2005/0091713 A1 | 4/2005 | Atkinson et al. |

FOREIGN PATENT DOCUMENTS

| WO | WO 01/37654 | * 5/2001 |
| WO | WO 01/96584 | * 12/2001 |
| WO | WO 03/052110 A2 | 6/2006 |

OTHER PUBLICATIONS

Hussey et al. Braz. J. Plant Physiol., 14(3): 183-194 (2002).*
Wrather et al., 1994. Plant Disease 81:107-110.
Sim et al., Plant Disease 70:603 (1986).
Todd et al., Nematology 27:628-633 (1995).
Young, Supplement to the Journal of Nematology 30:525-529 (1998).
Guo et al., 1995, Cell, 81 (4) 611-620.
Fire et al., 1998, Nature 391: 806-811.
Carthew, Curr. Opin. Cell Biol. 13(2):244-248 (2001).
Fraser et al., . Nature 408, 325-330 (2000).
Gonczy et al., Nature 408, 331-336 (2000).
Maeda et al., Curr Biol 11, 171-176 (2001).
Bird, D.M., et al.; "NCBI, GenBank, Accession No. AAA28126"; (Apr. 26, 1993), (pp. 1-2.
Wilson, R., et al.; "NCBI, GenBank, Accession No. AF026210"; (Sep. 25, 1997), (pp. 1-13.
Boutla, Alexandra, et al.; "Induction of RNA interference in Caenorhabditis elegans by RNA's derived from plants exhibiting post-transcriptional gene silencing"; Nucleic Acids Research, (2002); vol. 30, No. 7, (pp. 1688-1694.
Klass, M.R.,et al.; "NCBI, GenBank, Accession No. K02618"; (Apr. 26, 1993), (pp.) 1-2.
Valvekens, Dirk, et al.; "Agrobacterium tumefaciens-mediated transformation of *Arabidopsis thaliana* root explants by using kanamycin selection"; Proc. Natl. Acad. Sci., (Aug. 1988); vol. 85, (pp.) 5536-5540.
Urwin, P.E., et al.; "Ingestion of Double-Stranded RNA by Preparasitic Juvenile Cyst Nematodes Leads to RNA Interference"; MPMI, (2002); vol. 15, No. 8, (pp.) 747-752.
Klass, Michael R., et al.; "Isolation and Characterization of a Sperm-Specific Gene Family in the Nematode Caenorhabditis elegans"; Molecular and Cellular Biology, (Mar. 1984); vol. 4, No. 3, (pp. 529-537.
Dalley, Brian K., et al.; "Post-Transcriptional Regulation of RNA Polymerase II Levels in Caenorhabditis elgans"; Genetics, (Feb. 1993); vol. 133, (pp.) 237-245.
Veronico, P., et al.; "Nematode chitin synthases: gene structure, expression and function in Caenorhabditis elegans and the plant parasitic nematode meloidogyne artiellia"; Mol. Genet Genomics, (2001); vol. 266, (pp.) 28-34.
Sijen, Titia, et al.; "On the Role of RNA Amplification in dsRNA-Triggered Gene Silencing"; Cell, (Nov. 16, 2001); vol. 107, (pp.) 465-476.
Fanelli, Elena, et al.; "Analysis of chitin synthase function in a plant parasitic nematode, Meloidogyne artiellia, using RNAi"; Gene, Elsevier Science (2005); vol. 349, (pp.) 87-95.
Piano et al., Current Biology 10:1619-1622 (2000).

* cited by examiner

*Primary Examiner*—Medina A Ibrahim
(74) *Attorney, Agent, or Firm*—Casimir Jones, S.C.

(57) ABSTRACT

The present invention relates to compositions and methods for controlling nematode infestation of plants. In particular, the present invention provides vectors comprising sequences designed to control nematodes by RNA interference (RNAi) and transgenic plants transformed with such vectors.

17 Claims, 17 Drawing Sheets

Figure 1

SEQ ID NO:1

GATGANCATTTATTAACGCACAACAACAATACAATTACATANGGCAACAATCAAATATA
CATTCATTTGAAGTGATGATCACAGAAATTTACATACAGATACAACAATTTACATGATG
GGGGACAAAATGACAATTTTGGGACGGTGGGATGGGATCCTATCATGTCCATGTTGAGG
TGACGAAGCATCCTTCCATCAGACGTTGTACTCGATCGGCAAGTTCTTGCGGCGCACCA
TCCCGTCTCCCTGGAACCACTCGAGCTTGAACGTGGTGTCGGCTGGGTCCGGTGTGTTG
GTCCACTCCGCGGCGGCGGCGGCGCCGGGCGGTTCCGGCACGTTGGTCCACGCCACGGT
CACACGGTCGTCCTTGGTGTCCTCGCTGCCGGGGTCGAAGGCGTCNCAGAANACGGCCA
CGTTGACAGATTCCTTTGGGCCGANCACTCCGTCCGGCGGGTTCATGTTGATNCGCTTC
GGTTTGGTGGTCTTGAAGGCGTAGCCGATGCGCTTCGTCCCAAGGTTGATCACNCNCAA
GTAGTANATGGCTTTGTTGTCGAAGGNACGTTGNAANAGATCTTCTGCGTGGGCATTGT
TGCGACGTCCTCTGGTGGAAGTTGCGCCATTGCTGTTGTTGTCGCTGTTGTCGGGCTGG
CTTTGTGGGTGCTTGATGTGTGATCGTTGAGAGCGTTGCTTGAAGTGTTGCTGCTATGC
TGCTGAGTGAGGGGAATGTGCAAAATCCACCTCCTTATATACAAAATTCGGGTGCAAAA
ATTCATGCAGCAAAAAAAAGTGTATAAAAGGCGACGGTTTTCTTCACTTTTCACCAGT
GCCAGCCAGCCTTCAACTCAACGCAACATCAACACCAGTGCGCGCCAAGCTCGTCTACA
CATTTCGTCGCGACAACTCATCACTGATCACAGAAATTTACATACAGATACAACAATTT
ACATGATGGGGGACAAAATGACAATTTTGGGACGGTGGGATGGGATCCTATCATGTCCA
TGTTGAGGTGACGAAGCATCCTTCCATCAGACGTTGTACTCGATCGGCAAGTTCTTGCG
GCGCACCATCCCGTCTCCCTGGAACCACTCGAGCTTGAACGCGGTGACCGGCAGGGCCC
GGCGTGTTGGTCCACTCCACGGCGGCGGTGGCGCCGGGAGGCTNCNCGTGTTGGTCCAC
TCCACGGTCACACGGTCGCCCTTGGGTGTCCTCGCTTNACCTNCNTNTNCGTTTNNNNT
GNTATTTTGCCGNACTGN

Figure 2A

SEQ ID NO:4

C'TCGAGCTTGAACGTGGTGTCGGCTGGGTCCGGTGTGTTGGTCCACTCCGCGGCGGCG
GCGGCGCCGGGCGGTTCCGGCACGTTGGTCCACGCCACGGTCACACGGTCGTCCTTGGT
GTCCTCGCTGCCGGGGTCGAAGGCGTCNCAGAANACGGCCACGTTGACAGATTCCTTTG
GGCCGANCACTCCGTCCGGCGGGTTCATGTTGATNCGCTTCGGTTTGGTGGTCTTGAAG
GCCTGCA'G

Figure 2B

SEQ ID NO:45

G'GATCCTATCATGTCCATGTTGAGGTGACGAAGCATCCTTCCATCAGACGTT
GTACTCGATCGGCAAGTTCTTGCGGCGCACCATCCCGTCTCCCTGGAACCACT
CGAGCTTGAACGTGGTGTCGGCTGGGTCCGGTGTGTTGGTCCACTCCGCGGC
GGCGGCGGCGCCGGGCGGTTCCGGCACGTTGGTCCACGCCACGGTCACACGG
TCGTCCTTGGTGTCCTCGCTGCCGGGGTCGAAGGCGTCNCAGAANACGGCCA
CGTTGACAGATTCCTTTGGGCCGANCACTCCGTCCGGCGGGTTCATGTTGATN
CGCTTCGGTTTGGTGGTCTTGAAGGCCTGCAGCCATGGNNNNNNNNNNNNNNN
NNNNNNNNNNNNNNNNNG'AATTC

Figure 3

SEQ ID NO:5

```
CTGCA' GGCCTTCAAGACCACCAAACCGAAGCGNATCAACATGAACCCGCC
GGACGGAGTGNTCGGCCCAAAGGAATCTGTCAACGTGGCCGTNTTCTGNG
ACGCCTTCGACCCCGGCAGCGAGGACACCAAGGACGACCGTGTGACCGTG
GCGTGGACCAACGTGCCGGAACCGCCCGGCGCCGCCGCCGCGGAGTG
GACCAACACACCGGACCCAGCCGACACCACGTTCAAGC' TCGAG
```

Figure 4

SEQ ID NO:6

AAGCTTGCATGCCTGCA'GGCCTTCAAGACCACCAAACCGAAGCGNATCAACATGAACC
CGCCGGACGGAGTGNTCGGCCCAAAGGAATCTGTCAACGTGGCCGTNTTCTGNGACGCC
TTCGACCCCGGCAGCGAGGACACCAAGGACGACCGTGTGACCGTGGCGTGGACCAACGT
GCCGGAACCGCCCGGCGCCGCCGCCGCCGCGGAGTGGACCAACACACCGGACCCAGCCG
ACACCACGTTCAAGC'TCGACTCTAGAG'GATCCTATCATGTCCATGTTGAGGTGACGA
AGCATCCTTCCATCAGACGTTGTACTCGATCGGCAAGTTCTTGCGGCGCACCATCCCGT
CTCCCTGGAACCACTCGAGCTTGAACGTGGTGTCGGCTGGGTCCGGTGTGTTGGTCCAC
TCCGCGGCGGCGGCGCCGGGCGGTTCCGGCACGTTGGTCCACGCCACGGTCACACG
GTCGTCCTTGGTGTCCTCGCTGCCGGGGTCGAAGGCGTCNCAGAANACGGCCACGTTGA
CAGATTCCTTTGGGCCGANCACTCCGTCCGGCGGGTTCATGTTGATNCGCTTCGGTTTG
GTGGTCTTGAAGGCCTGCAGCCATGG

Figure 5

SEQ ID NO:9

5'-
CCAACCCTGCACAAAATGCTATGATGGGACATCGTGTTAAGGCATGACTGTT
TTATTTGCAATTGTTATTTTGGATTATTACGATAGATCTTACCTTGGTCGACTT
TTCGTATGAATTTGTCCGTCACAACCCCTTACAATGCTGATTTTGACGGGGAT
GAAATGAATTAGCACCTTCCGCAATCACTGGAGACACGGGCAGAAATAAACG
AAATTGCGATGGTTTTTATTAATTTAAAGCACCAAATATAACCCTTACCTTTT
CTCTAAAAAGGCATCTCGACAGTTAATTACGCCACAGGCCAACAAGCCAGTG
ATGGGAATTGTGCAGGACACATTGACCGCAGTTCGAATGATGACTAAACGCG
ACGTTTTATTGATTACGCTCGTCTCATGGATTTGTTGATGCATTTGCCAAATT
GGGATGGAAAAATTCCGCAGCCAGCGATAATCAAACCCAAGCCACTTTGGAC
CGGAAAACAAGTGTTTACAAAGATAATTCCAGGTTTTGTCAAATGAAACTTTT
CCTCCATTCTTTGTTTTGTTCTAACTAAGGCAGTGTCAATGTTATCCGAACAC
ATTCGACCCATCCGGACGACGAAGACAGCGGACCATACAAATGGATTTCCCC
TGGCGACACCAAAGTGCTCATTGAGAACAGCGAACTTCTCTCTGGGATAATT
TGTTCCAAAACTGTTGGCAGAGGTTCCNGAAACCTTCTTCACATTGTCGCATT
AGAATTGGGTCATCAAATTGCTGCCGAGTTATATGCCAACATACAAACTGTT
ATAAACGCATGGCTTCTCGCCGAGGGACACACCATTGGAATTGGTTTCCAATT
TTACTTTTATTTACAATAATTTTGTTTAACTCTCAGGTGACACAATTGCTGATA
CTTCCACCTACAGAGATATCCAGGAGACCATAAGAAAGGCCAAACAGGATGT
CATTGATGTTATCGAGAAAGCTCACAACGATGATNCTCGAGCCGACTNCCCG
GGAACACACTTCGACAGACTTCGAAAATCAAGTGAACCGAATTNCTG-3'

Figure 6
SEQ ID NO:10

5'-
GGCAGTGTCAATGTTATCCGAACACATTCGACCCATCCGGACGACGAAGACA
GCGGACCATACAAATGGATTTCCCCTGGCGACACCAAAGTGCTCATTGAGAA
CAGCGAACTTCTCTCTGGGATAATTTGTTCCAAAACTGTTGGCAGAGGTTCCN
GAAACCTTCTTCACATTGTCGCATTAGAATTGGGTCATCAAATTGCTGCCGAG
TTATATGCCAACATACAAACTGTTATAAACGCATGGCTTCTCGCCGAGGGAC
ACACCATTGGAATTGGT-3'

Figure 7

SEQ ID NO:13

Antisense fragment-285bp
279bp exon region from above showing the RP2_KpnF1B and RP2_BamRB primers:

5'-
GGCAGTGTCAATGTTATCCGAACACATTCGACCCATCCGGACGACGAAGACA
GCGGACCATACAAATGGATTTCCCCTGGCGACACCAAAGTGCTCATTGAGAA
CAGCGAACTTCTCTCTGGGATAATTTGTTCCAAAACTGTTGGCAGAGGTTCCN
GAAACCTTCTTCACATTGTCGCATTAGAATTGGGTCATCAAATTGCTGCCGAG
TTATATGCCAACATACAAACTGTTATAAACGCATGGCTTCTCGCCGAGGGAC
ACACCATTGGAATTGGT-3'

Figure 8
SEQ ID NO:14

Reverse complement of the 279bp exon fragment showing the RP2_KpnF1B and RP2_BamRB primers:

5'-
ACCAATTCCAATGGTGTGTCCCTCGGCGAGAAGCCATGCGTTTATAACAGTTT
GTATGTTGGCATATAACTCGGCAGCAATTTGATGACCCAATTCTAATGCGACA
ATGTGAAGAAGGTTTCNGGAACCTCTGCCAACAGTTTTGGAACAAATTATCC
CAGAGAGAAGTTCGCTGTTCTCAATGAGCACTTTGGTGTCGCCAGGGGAAAT
CCATTTGTATGGTCCGCTGTCTTCGTCGTCCGGATGGGTCGAATGTGTTCGGA
TAACATTGACACTGCC-3'

Cloning strategy for sense RNA polymerase II sequence

Figure 10

SEQ ID NO:17

GGCAGTGTCAATGTTATCCGAACACATTCGACCCATCCGGACGACGAAG
ACAGCGGACCATACAAATGGATTTCCCCTGGCGACACCAAAGTGCTCATTGA
GAACAGCGAACTTCTCTCTGGGATAATTTGTTCCAAAACTGTTGGCAGAGGTT
CCNGAAACCTTCTTCACATTGTCGCATTAGAATTGGGTCATCAAATTGCTGCC
GAGTTATATGCCAACATACAAACTGTTATAAACGCATGGCTTCTCGCCGAGG
GACACACCATTGGAATTGGT

Cloning strategy for sense RNA polymerase II sequence

Figure 12

SEQ ID NO:18

Sp6-
CAAGAAACGATGGTCCCAGGTGATGTACATGTACTTTTTGCTCGGGCATCGAATTATGG
ACTCACATTTGAGCGTAGAAGACAAACAATTGCAGGTCTTTTGAGCCTAAATTTTGCCC
TCGTGGAATCTGTGCAATAATTCAATGTTCGCACCGATGCTTAGGCTGACAACACATAT
ATTCTCGCCATTGATGGCGATTCCAAATTCGAACCAGCGGCAGTGATTCGTCTTTTACA
TCTGATGAACTTGAAAAGCGACGTTGGCTGTGCGTGCGGAAGAATCCATCCGATTGGAG
AAGGTGTGCTATCCTTCCCATTAATGGTGAATTTCTTACCATTCCCCAGGGGTC<u>ATGGT</u>
<u>TTGGTACCAAAAGTTCGAGTACGCAATCGCCCATTGGTTCCAAAAGGCTGCTGAGCATG</u>
<u>TGTTCGGCTGTGTTTTGTGTGCCCCCGGTAGCTTCTCTCTGTTTCGTGCTTCTGCTCTC</u>
<u>ATGGATGACAATGTGATGCACAAATACACCAAAANTGCCTCCGAACCNACGACNATTTT</u>
<u>GTTCAGTATGATCAAGGCGAAGACCCGATGGA</u>-T7

Figure 13. Soybean cyst production on transgenic lines vs. control plants as functional of cysts per plant.
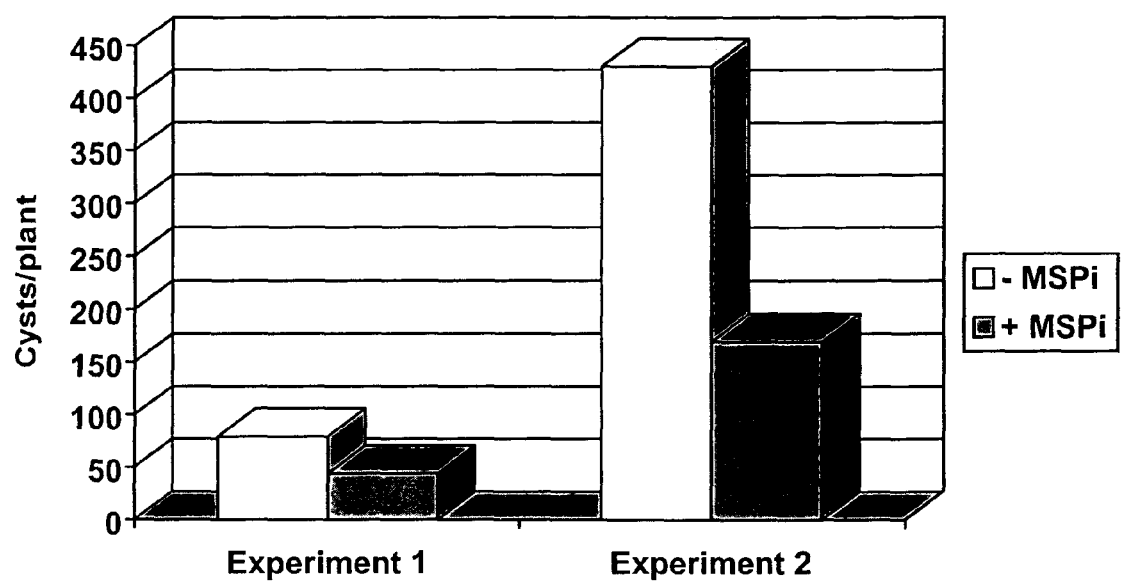

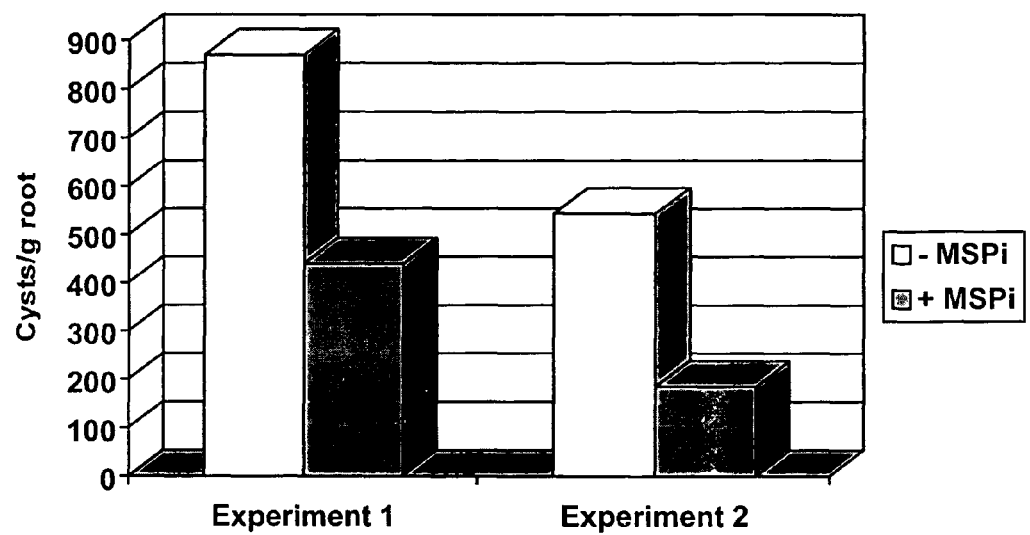
Figure 14. Soybean cyst production on transgenic lines vs. control plants as functional of cysts per gram of root tissue. "*" indicates data is significant.

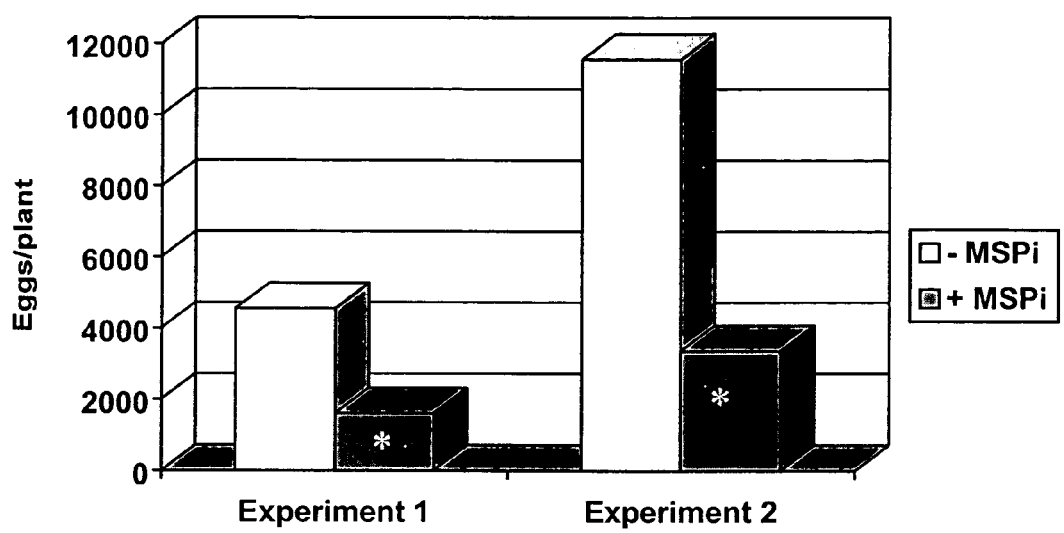
Figure 15. Soybean cyst nematode egg production on transgenic lines vs. control plants as an average number of eggs per plant. "*" indicates data is significant.

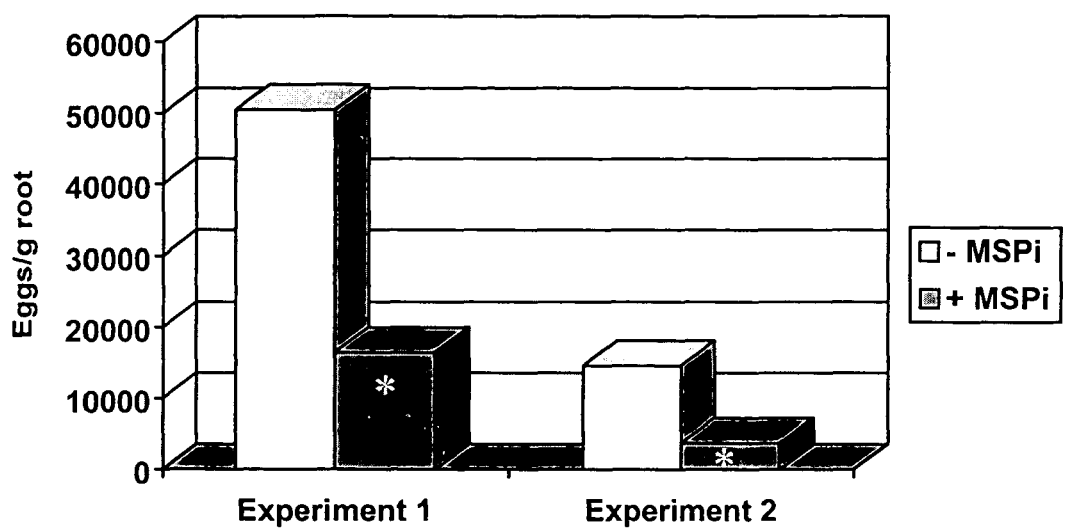
Figure 16. Soybean cyst nematode egg production on transgenic lines vs. control plants as an average number of eggs per gram of root. "*" indicates data is significant.

Figure 17. Soybean cyst nematode egg production on transgenic lines vs. control plants as an average number of eggs per cyst.

SEQUENCE LISTING

```
<160> NUMBER OF SEQ ID NOS: 45

<210> SEQ ID NO 1
<211> LENGTH: 1257
<212> TYPE: DNA
<213> ORGANISM: Heterodera glycines
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (400)..(400)
<223> OTHER INFORMATION: n is a, c, g, or t
<220> FEATURE:
<221> NAME/KEY: misc_feature
<222> LOCATION: (406)..(406)
<223> OTHER INFORMATION: n is a, c, g, or t
<220> FEATURE:
<221> NAME/KEY: misc_feature
<222> LOCATION: (438)..(438)
<223> OTHER INFORMATION: n is a, c, g, or t
<220> FEATURE:
<221> NAME/KEY: misc_feature
<222> LOCATION: (466)..(466)
<223> OTHER INFORMATION: n is a, c, g, or t
<220> FEATURE:
<221> NAME/KEY: misc_feature
<222> LOCATION: (526)..(526)
<223> OTHER INFORMATION: n is a, c, g, or t
<220> FEATURE:
<221> NAME/KEY: misc_feature
<222> LOCATION: (528)..(528)
<223> OTHER INFORMATION: n is a, c, g, or t
<220> FEATURE:
<221> NAME/KEY: misc_feature
<222> LOCATION: (538)..(538)
<223> OTHER INFORMATION: n is a, c, g, or t
<220> FEATURE:
<221> NAME/KEY: misc_feature
<222> LOCATION: (558)..(558)
<223> OTHER INFORMATION: n is a, c, g, or t
<220> FEATURE:
<221> NAME/KEY: misc_feature
<222> LOCATION: (565)..(565)
<223> OTHER INFORMATION: n is a, c, g, or t
<220> FEATURE:
<221> NAME/KEY: misc_feature
<222> LOCATION: (568)..(568)
<223> OTHER INFORMATION: n is a, c, g, or t
<220> FEATURE:
<221> NAME/KEY: misc_feature
<222> LOCATION: (1165)..(1165)
<223> OTHER INFORMATION: n is a, c, g, or t
<220> FEATURE:
<221> NAME/KEY: misc_feature
<222> LOCATION: (1167)..(1167)
<223> OTHER INFORMATION: n is a, c, g, or t
```

```
<220> FEATURE:
<221> NAME/KEY: misc_feature
<222> LOCATION: (1218)..(1218)
<223> OTHER INFORMATION: n is a, c, g, or t
<220> FEATURE:
<221> NAME/KEY: misc_feature
<222> LOCATION: (1223)..(1223)
<223> OTHER INFORMATION: n is a, c, g, or t
<220> FEATURE:
<221> NAME/KEY: misc_feature
<222> LOCATION: (1225)..(1225)
<223> OTHER INFORMATION: n is a, c, g, or t
<220> FEATURE:
<221> NAME/KEY: misc_feature
<222> LOCATION: (1227)..(1227)
<223> OTHER INFORMATION: n is a, c, g, or t
<220> FEATURE:
<221> NAME/KEY: misc_feature
<222> LOCATION: (1229)..(1229)
<223> OTHER INFORMATION: n is a, c, g, or t
<220> FEATURE:
<221> NAME/KEY: misc_feature
<222> LOCATION: (1235)..(1238)
<223> OTHER INFORMATION: n is a, c, g, or t
<220> FEATURE:
<221> NAME/KEY: misc_feature
<222> LOCATION: (1241)..(1241)
<223> OTHER INFORMATION: n is a, c, g, or t
<220> FEATURE:
<221> NAME/KEY: misc_feature
<222> LOCATION: (1252)..(1252)
<223> OTHER INFORMATION: n is a, c, g, or t
<220> FEATURE:
<221> NAME/KEY: misc_feature
<222> LOCATION: (1257)..(1257)
<223> OTHER INFORMATION: n is a, c, g, or t

<400> SEQUENCE: 1
gatgancatt tattaacgca caacaacaat acaattacat anggcaacaa tcaaatatac      60
attcatttga agtgatgatc acagaaattt acatacagat acaacaattt acatgatggg     120
ggacaaaatg acaattttgg gacggtggga tgggatccta tcatgtccat gttgaggtga     180
cgaagcatcc ttccatcaga cgttgtactc gatcggcaag ttcttgcggc gcaccatccc     240
gtctccctgg aaccactcga gcttgaacgt ggtgtcggct gggtccggtg tgttggtcca     300
ctccgcggcg gcggcggcgc cgggcggttc cggcacgttg gtccacgcca cggtcacacg     360
gtcgtccttg gtgtcctcgc tgccggggtc gaaggcgtcn cagaanacgg ccacgttgac     420
agattccttt gggccganca ctccgtccgg cgggttcatg ttgatncgct tcggttttggt     480 ggtcttgaag gcgtagccga tgcgcttcgt cccaaggttg atcacncnca agtagtanat     540
ggctttgttg tcgaaggnac gttgnaanag atcttctgcg tgggcattgt tgcgacgtcc     600
tctggtggaa gttgcgccat tgctgttgtt gtcgctgttg tcgggctggc tttgtgggtg     660
cttgatgtgt gatcgttgag agcgttgctt gaagtgttgc tgctatgctg ctgagtgagg     720
ggaatgtgca aaatccacct ccttatatac aaaattcggg tgcaaaaatt catgcagcaa     780
aaaaaaagtg tataaaaggc gacggttttc ttcactttc accagtgcca gccagccttc      840
aactcaacgc aacatcaaca ccagtgcgcg ccaagctcgt ctacacattt cgtcgcgaca     900
actcatcact gatcacagaa atttacatac agatacaaca atttacatga tggggacaa     960 aatgacaatt tgggacggt gggatgggat cctatcatgt ccatgttgag gtgacgaagc    1020
atccttccat cagacgttgt actcgatcgg caagttcttg gcgcacca tcccgtctcc     1080 ctggaaccac tcgagcttga acgcggtgac cggcagggcc cggcgtgttg gtccactcca    1140
cggcggcggt ggcgccggga ggctncncgt gttggtccac tccacggtca cacggtcgcc    1200
```

-continued cttgggtgtc ctcgcttnac ctncntntnc gtttnnnntg ntattttgcc gnactgn      1257

<210> SEQ ID NO 2
<211> LENGTH: 22
<212> TYPE: DNA
<213> ORGANISM: Artificial Sequence
<220> FEATURE:
<223> OTHER INFORMATION: Synthetic

<400> SEQUENCE: 2
gtaatacgac tcactatagg gc                                           22

<210> SEQ ID NO 3
<211> LENGTH: 26
<212> TYPE: DNA
<213> ORGANISM: Artificial Sequence
<220> FEATURE:
<223> OTHER INFORMATION: Synthetic

<400> SEQUENCE: 3
ccatggctgc aggccttcaa gaccac                                       26

<210> SEQ ID NO 4
<211> LENGTH: 243
<212> TYPE: DNA
<213> ORGANISM: Heterodera glycines
<220> FEATURE:
<221> NAME/KEY: misc_feature
<222> LOCATION: (145)..(145)
<223> OTHER INFORMATION: n is a, c, g, or t
<220> FEATURE:
<221> NAME/KEY: misc_feature
<222> LOCATION: (151)..(151)
<223> OTHER INFORMATION: n is a, c, g, or t
<220> FEATURE:
<221> NAME/KEY: misc_feature
<222> LOCATION: (183)..(183)
<223> OTHER INFORMATION: n is a, c, g, or t
<220> FEATURE:
<221> NAME/KEY: misc_feature
<222> LOCATION: (211)..(211)
<223> OTHER INFORMATION: n is a, c, g, or t

<400> SEQUENCE: 4
ctcgagcttg aacgtggtgt cggctgggtc cggtgtgttg gtccactccg cggcggcggc    60
ggcgccgggc ggttccggca cgttggtcca cgccacggtc acacggtcgt ccttggtgtc   120
ctcgctgccg gggtcgaagg cgtcncagaa nacggccacg ttgacagatt cctttgggcc   180
gancactccg tccggcgggt tcatgttgat ncgcttcggt ttggtggtct tgaaggcctg   240
cag                                                                243

<210> SEQ ID NO 5
<211> LENGTH: 243
<212> TYPE: DNA
<213> ORGANISM: Heterodera glycines
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (93)..(93)
<223> OTHER INFORMATION: n is a, c, g, or t
<220> FEATURE:
<221> NAME/KEY: misc_feature
<222> LOCATION: (99)..(99)
<223> OTHER INFORMATION: n is a, c, g, or t

<400> SEQUENCE: 5

```
ctgcaggcct tcaagaccac caaaccgaag cgnatcaaca tgaacccgcc ggacggagtg    60
ntcggcccaa aggaatctgt caacgtggcc gtnttctgng acgccttcga ccccggcagc   120
gaggacacca aggacgaccg tgtgaccgtg gcgtggacca acgtgccgga accgcccggc   180
gccgccgccg ccgcggagtg gaccaacaca ccggacccag ccgacaccac gttcaagctc   240
gag                                                                 243
```

<210> SEQ ID NO 6
<211> LENGTH: 613
<212> TYPE: DNA
<213> ORGANISM: Heterodera glycines
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (73)..(73)
<223> OTHER INFORMATION: n is a, c, g, or t
<220> FEATURE:
<221> NAME/KEY: misc_feature
<222> LOCATION: (105)..(105)
<223> OTHER INFORMATION: n is a, c, g, or t
<220> FEATURE:
<221> NAME/KEY: misc_feature
<222> LOCATION: (111)..(111)
<223> OTHER INFORMATION: n is a, c, g, or t
<220> FEATURE:
<221> NAME/KEY: misc_feature
<222> LOCATION: (509)..(509)
<223> OTHER INFORMATION: n is a, c, g, or t
<220> FEATURE:
<221> NAME/KEY: misc_feature
<222> LOCATION: (515)..(515)
<223> OTHER INFORMATION: n is a, c, g, or t
<220> FEATURE:
<221> NAME/KEY: misc_feature
<222> LOCATION: (547)..(547)
<223> OTHER INFORMATION: n is a, c, g, or t
<220> FEATURE:
<221> NAME/KEY: misc_feature
<222> LOCATION: (575)..(575)
<223> OTHER INFORMATION: n is a, c, g, or t

<400> SEQUENCE: 6

```
aagcttgcat gcctgcaggc cttcaagacc accaaaccga agcgnatcaa catgaacccg    60
ccggacggag tgntcggccc aaaggaatct gtcaacgtgg ccgtnttctg ngacgccttc   120
gaccccggca gcgaggacac caaggacgac cgtgtgaccg tggcgtggac caacgtgccg   180
gaaccgcccg gcgccgccgc cgccgcggag tggaccaaca caccggaccc agccgacacc   240
acgttcaagc tcgactctag aggatcctat catgtccatg ttgaggtgac gaagcatcct   300
tccatcagac gttgtactcg atcggcaagt tcttgcggcg caccatcccg tctccctgga   360
accactcgag cttgaacgtg gtgtcggctg gtccggtgt gttggtccac tccgcggcgg   420
cggcggcgcc gggcggttcc ggcacgttgg tccacgccac ggtcacacgg tcgtccttgg   480
tgtcctcgct gccggggtcg aaggcgtcnc agaanacggc cacgttgaca gattcctttg   540
ggccgancac tccgtccggc gggttcatgt tgatncgctt cggtttggtg gtcttgaagg   600
cctgcagcca tgg                                                     613
```

<210> SEQ ID NO 7

```
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (21)..(21)
<223> OTHER INFORMATION: n is a, c, g, or t

<400> SEQUENCE: 7
ccaaccctgc acaaaatgws natgatg                                              27

<210> SEQ ID NO 8
<211> LENGTH: 27
<212> TYPE: DNA
<213> ORGANISM: Artificial Sequence
<220> FEATURE:
<223> OTHER INFORMATION: Synthetic

<400> SEQUENCE: 8
cagaattcgg ttcacttgrt tytcraa                                              27

<210> SEQ ID NO 9
<211> LENGTH: 1047
<212> TYPE: DNA
<213> ORGANISM: Heterodera glycines
<220> FEATURE:
<221> NAME/KEY: misc_feature
<222> LOCATION: (712)..(712)
<223> OTHER INFORMATION: n is a, c, g, or t
<220> FEATURE:
<221> NAME/KEY: misc_feature
<222> LOCATION: (983)..(983)
<223> OTHER INFORMATION: n is a, c, g, or t
<220> FEATURE:
<221> NAME/KEY: misc_feature
<222> LOCATION: (996)..(996)
<223> OTHER INFORMATION: n is a, c, g, or t
<220> FEATURE:
<221> NAME/KEY: misc_feature
<222> LOCATION: (1044)..(1044)
<223> OTHER INFORMATION: n is a, c, g, or t

<400> SEQUENCE: 9
ccaaccctgc acaaaatgct atgatgggac atcgtgttaa ggcatgactg ttttatttgc          60
aattgttatt ttggattatt acgatagatc ttaccttggt cgacttttcg tatgaatttg         120
tccgtcacaa ccccttacaa tgctgatttt gacggggatg aaatgaatta gcaccttccg         180
caatcactgg agacacgggc agaaataaac gaaattgcga tggtttttat taatttaaag         240
caccaaatat aaccCttacc ttttctctaa aaaggcatct cgacagttaa ttacgccaca         300
ggccaacaag ccagtgatgg gaattgtgca ggacacattg accgcagttc gaatgatgac         360
taaacgcgac gttttattg attacgctcg tctcatggat tgttgatgc atttgccaaa          420 ttgggatgga aaaattccgc agccagcgat aatcaaaccc aagccacttt ggaccggaaa         480
acaagtgttt acaagataa ttccaggttt tgtcaaatga aacttttcct ccattctttg          540
ttttgttcta actaaggcag tgtcaatgtt atccgaacac attcgaccca tccggacgac         600
gaagacagcg gaccatacaa atggatttcc cctggcgaca ccaaagtgct cattgagaac         660
agcgaacttc tctctgggat aatttgttcc aaaactgttg gcagaggttc cngaaacctt         720
cttcacattg tcgcattaga attgggtcat caaattgctg ccgagttata tgccaacata         780
caaactgtta taaacgcatg gcttctcgcc gagggacaca ccattggaat tggtttccaa         840
ttttactttt atttacaata attttgttta actctcaggt gacacaattg ctgatacttc         900
```

```
cacctacaga gatatccagg agaccataag aaaggccaaa caggatgtca ttgatgttat      960
cgagaaagct cacaacgatg atnctcgagc cgactnccg  ggaacacact tcgacagact     1020
tcgaaaatca agtgaaccga attnctg                                         1047

<210> SEQ ID NO 10
<211> LENGTH: 279
<212> TYPE: DNA
<213> ORGANISM: Heterodera glycines
<220> FEATURE:
<221> NAME/KEY: misc_feature
<222> LOCATION: (157)..(157)
<223> OTHER INFORMATION: n is a, c, g, or t

<400> SEQUENCE: 10
ggcagtgtca atgttatccg aacacattcg acccatccgg acgacgaaga cagcggacca       60
tacaaatgga tttcccctgg cgacaccaaa gtgctcattg agaacagcga acttctctct      120
gggataattt gttccaaaac tgttggcaga ggttccngaa accttcttca cattgtcgca      180
ttagaattgg gtcatcaaat tgctgccgag ttatatgcca acatacaaac tgttataaac      240
gcatggcttc tcgccgaggg acacaccatt ggaattggt                             279

<210> SEQ ID NO 11
<211> LENGTH: 32
<212> TYPE: DNA
<213> ORGANISM: Artificial Sequence
<220> FEATURE:
<223> OTHER INFORMATION: Synthetic

<400> SEQUENCE: 11
gacggtaccg gcagtgtcaa tgttatccga ac                                    32

<210> SEQ ID NO 12
<211> LENGTH: 29
<212> TYPE: DNA
<213> ORGANISM: Artificial Sequence
<220> FEATURE:
<223> OTHER INFORMATION: Synthetic

<400> SEQUENCE: 12
atcggatcct ccaatggtgt gtccctcgg                                        29

<210> SEQ ID NO 13
<211> LENGTH: 279
<212> TYPE: DNA
<213> ORGANISM: Heterodera glycines
<220> FEATURE:
<221> NAME/KEY: misc_feature
<222> LOCATION: (157)..(157)
<223> OTHER INFORMATION: n is a, c, g, or t

<400> SEQUENCE: 13
ggcagtgtca atgttatccg aacacattcg acccatccgg acgacgaaga cagcggacca       60
tacaaatgga tttcccctgg cgacaccaaa gtgctcattg agaacagcga acttctctct      120
gggataattt gttccaaaac tgttggcaga ggttccngaa accttcttca cattgtcgca      180
ttagaattgg gtcatcaaat tgctgccgag ttatatgcca acatacaaac tgttataaac      240
gcatggcttc tcgccgaggg acacaccatt ggaattggt                             279

<210> SEQ ID NO 14
<211> LENGTH: 279
<212> TYPE: DNA
```

```
<213> ORGANISM: Heterodera glycines
<220> FEATURE:
<221> NAME/KEY: misc_feature
<222> LOCATION: (123)..(123)
<223> OTHER INFORMATION: n is a, c, g, or t

<400> SEQUENCE: 14
accaattcca atggtgtgtc cctcggcgag aagccatgcg tttataacag tttgtatgtt    60
ggcatataac tcggcagcaa tttgatgacc caattctaat gcgacaatgt gaagaaggtt   120
tcnggaacct ctgccaacag ttttggaaca aattatccca gagagaagtt cgctgttctc   180
aatgagcact tggtgtcgc caggggaaat ccatttgtat ggtccgctgt cttcgtcgtc   240
cggatgggtc gaatgtgttc ggataacatt gacactgcc                          279

<210> SEQ ID NO 15
<211> LENGTH: 30
<212> TYPE: DNA
<213> ORGANISM: Artificial Sequence
<220> FEATURE:
<223> OTHER INFORMATION: Synthetic

<400> SEQUENCE: 15
tgaggtaccg acgaagacag cggaccatac                                     30

<210> SEQ ID NO 16
<211> LENGTH: 29
<212> TYPE: DNA
<213> ORGANISM: Artificial Sequence
<220> FEATURE:
<223> OTHER INFORMATION: Synthetic

<400> SEQUENCE: 16
ttcgagctct ccaatggtgt gtccctcgg                                      29

<210> SEQ ID NO 17
<211> LENGTH: 279
<212> TYPE: DNA
<213> ORGANISM: Heterodera glycines
<220> FEATURE:
<221> NAME/KEY: misc_feature
<222> LOCATION: (157)..(157)
<223> OTHER INFORMATION: n is a, c, g, or t

<400> SEQUENCE: 17
ggcagtgtca atgttatccg aacacattcg acccatccgg acgacgaaga cagcggacca    60
tacaaatgga tttcccctgg cgacaccaaa gtgctcattg agaacagcga acttctctct   120
gggataattt gttccaaaac tgttggcaga ggttccngaa accttcttca cattgtcgca   180
ttagaattgg gtcatcaaat tgctgccgag ttatatgcca acatacaaac tgttataaac   240
gcatggcttc tcgccgaggg acacaccatt ggaattggt                          279

<210> SEQ ID NO 18
<211> LENGTH: 563
<212> TYPE: DNA
<213> ORGANISM: Heterodera glycines
<220> FEATURE:
<221> NAME/KEY: misc_feature
<222> LOCATION: (507)..(507)
<223> OTHER INFORMATION: n is a, c, g, or t
<220> FEATURE:
<221> NAME/KEY: misc_feature
<222> LOCATION: (520)..(520)
<223> OTHER INFORMATION: n is a, c, g, or t
<220> FEATURE:
<221> NAME/KEY: misc_feature
```

```
<222> LOCATION: (526)..(526)
<223> OTHER INFORMATION: n is a, c, g, or t

<400> SEQUENCE: 18
caagaaacga tggtcccagg tgatgtacat gtacttttg ctcgggcatc gaattatgga     60
ctcacatttg agcgtagaag acaaacaatt gcaggtcttt tgagcctaaa ttttgccctc   120
gtggaatctg tgcaataatt caatgttcgc accgatgctt aggctgacaa cacatatatt   180
ctcgccattg atggcgattc caaattcgaa ccagcggcag tgattcgtct tttacatctg   240
atgaacttga aaagcgacgt tggctgtgcg tgcggaagaa tccatccgat tggagaaggt   300
gtgctatcct tcccattaat ggtgaatttc ttaccattcc ccagggtca tggtttggta    360 ccaaaagttc gagtacgcaa tcgcccattg gttccaaaag ctgctgagc atgtgttcgg    420 ctgtgttttg tgtgccccg gtagcttctc tctgtttcgt gcttctgctc tcatggatga    480
caatgtgatg cacaaataca ccaaaantgc ctccgaaccn acgacnattt tgttcagtat   540
gatcaaggcg aagcccgat gga                                            563

<210> SEQ ID NO 19
<211> LENGTH: 17
<212> TYPE: DNA
<213> ORGANISM: Artificial Sequence
<220> FEATURE:
<223> OTHER INFORMATION: Synthetic

<400> SEQUENCE: 19
ccgatgctta ggctgac                                                   17

<210> SEQ ID NO 20
<211> LENGTH: 16
<212> TYPE: DNA
<213> ORGANISM: Artificial Sequence
<220> FEATURE:
<223> OTHER INFORMATION: Synthetic

<400> SEQUENCE: 20
ccagcggcag tgattc                                                    16

<210> SEQ ID NO 21
<211> LENGTH: 18
<212> TYPE: DNA
<213> ORGANISM: Artificial Sequence
<220> FEATURE:
<223> OTHER INFORMATION: Synthetic

<400> SEQUENCE: 21
agcacacctt ctccaatc                                                  18

<210> SEQ ID NO 22
<211> LENGTH: 21
<212> TYPE: DNA
<213> ORGANISM: Artificial Sequence
<220> FEATURE:
<223> OTHER INFORMATION: Synthetic

<400> SEQUENCE: 22
tggtaccaaa agttcgagta c                                              21

<210> SEQ ID NO 23
<211> LENGTH: 17
<212> TYPE: DNA
<213> ORGANISM: Artificial Sequence
<220> FEATURE:
```

<223> OTHER INFORMATION: Synthetic

<400> SEQUENCE: 23
catgtgttcg gctgtgt                                                17

<210> SEQ ID NO 24
<211> LENGTH: 17
<212> TYPE: DNA
<213> ORGANISM: Artificial Sequence
<220> FEATURE:
<223> OTHER INFORMATION: Synthetic

<400> SEQUENCE: 24
atcgggtctt cgccttg                                                17

<210> SEQ ID NO 25
<211> LENGTH: 62
<212> TYPE: DNA
<213> ORGANISM: Heterodera glycines
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (55)..(55)
<223> OTHER INFORMATION: n is a, c, g, or t

<400> SEQUENCE: 25
cggggtcgaa ggcgtcncag aanacggcca cgttgacaga ttcctttggg ccgancactc    60
cg                                                                  62

<210> SEQ ID NO 26
<211> LENGTH: 33
<212> TYPE: DNA
<213> ORGANISM: Heterodera glycines
<220> FEATURE:
<221> NAME/KEY: misc_feature
<222> LOCATION: (21)..(21)
<223> OTHER INFORMATION: n is a, c, g, or t

<400> SEQUENCE: 26
tccggcgggt tcatgttgat ncgcttcggt ttg                              33

<210> SEQ ID NO 27
<211> LENGTH: 39
<212> TYPE: DNA
<213> ORGANISM: Heterodera glycines

<400> SEQUENCE: 27
cgtggtgtcg gctgggtccg gtgtgttggt ccactccgc                        39

<210> SEQ ID NO 28
<211> LENGTH: 52
<212> TYPE: DNA
<213> ORGANISM: Heterodera glycines

<400> SEQUENCE: 28
ggcacgttgg tccacgccac ggtcacacgg tcgtccttgg tgtcctcgct gc          52

<210> SEQ ID NO 29
<211> LENGTH: 52

```
<212> TYPE: DNA
<213> ORGANISM: Heterodera glycines
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t

<400> SEQUENCE: 29
ggcgtcncag aaacggcca cgttgacaga ttcctttggg ccgancactc cg         52

<210> SEQ ID NO 30
<211> LENGTH: 62
<212> TYPE: DNA
<213> ORGANISM: Heterodera glycines

<400> SEQUENCE: 30
gggcggttcc ggcacgttgg tccacgccac ggtcacacgg tcgtccttgg tgtcctcgct    60
gc                                                                  62

<210> SEQ ID NO 31
<211> LENGTH: 164
<212> TYPE: DNA
<213> ORGANISM: Heterodera glycines
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t

<400> SEQUENCE: 31
aatctgtcaa cgtggccgtn ttctgngacg ccttcgaccc cggcagcgag gacaccaagg    60
acgaccgtgt gaccgtggcg tggaccaacg tgccggaacc gcccggcgcc gccgccgccg  120
cggagtggac caacacaccg gacccagccg acaccacgtt caag                   164

<210> SEQ ID NO 32
<211> LENGTH: 119
<212> TYPE: DNA
<213> ORGANISM: Heterodera glycines
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (79)..(79)
<223> OTHER INFORMATION: n is a, c, g, or t
<220> FEATURE:
<221> NAME/KEY: misc_feature
<222> LOCATION: (107)..(107)
<223> OTHER INFORMATION: n is a, c, g, or t

<400> SEQUENCE: 32 ggtcgtccett ggtgtcctcg ctgccggggt cgaaggcgtc ncagaaacg gccacgttga    60
```

```
cagattcctt tgggccganc actccgtccg gcgggttcat gttgatncgc ttcggtttg    119
```

<210> SEQ ID NO 33
<211> LENGTH: 130
<212> TYPE: DNA
<213> ORGANISM: Heterodera glycines

<400> SEQUENCE: 33

```
ttgaacgtgg tgtcggctgg gtccggtgtg ttggtccact ccgcggcggc ggcggcgccg    60
ggcggttccg gcacgttggt ccacgccacg gtcacacggt cgtccttggt gtcctcgctg   120
ccggggtcga                                                          130
```

<210> SEQ ID NO 34
<211> LENGTH: 66
<212> TYPE: DNA
<213> ORGANISM: Heterodera glycines
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (47)..(47)
<223> OTHER INFORMATION: n is a, c, g, or t

<400> SEQUENCE: 34

```
ggtcgtcctt ggtgtcctcg ctgccggggt cgaaggcgtc ncagaanacg gccacgttga    60
cagatt                                                               66
```

<210> SEQ ID NO 35
<211> LENGTH: 128
<212> TYPE: DNA
<213> ORGANISM: Heterodera glycines
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (90)..(90)
<223> OTHER INFORMATION: n is a, c, g, or t

<400> SEQUENCE: 35

```
ttcaagacca ccaaaccgaa gcgnatcaac atgaacccgc cggacggagt gntcggccca    60
aaggaatctg tcaacgtggc cgtnttctgn gacgccttcg accccggcag cgaggacacc   120
aaggacga                                                            128
```

<210> SEQ ID NO 36
<211> LENGTH: 96
<212> TYPE: DNA
<213> ORGANISM: Heterodera glycines

<400> SEQUENCE: 36

```
ccgtgtgacc gtggcgtgga ccaacgtgcc ggaaccgccc ggcgccgccg ccgccgcgga    60
gtggaccaac acaccggacc cagccgacac cacgtt                              96
```

<210> SEQ ID NO 37
<211> LENGTH: 96
<212> TYPE: DNA
<213> ORGANISM: Heterodera glycines

<400> SEQUENCE: 37
atcatgtcca tgttgaggtg acgaagcatc cttccatcag acgttgtact cgatcggcaa    60
gttcttgcgg cgcaccatcc cgtctccctg aaacca                              96

<210> SEQ ID NO 38
<211> LENGTH: 50
<212> TYPE: DNA
<213> ORGANISM: Heterodera glycines

<400> SEQUENCE: 38
tggtttggta ccaaaagttc gagtacgcaa tcgcccattg gttccaaaag               50

<210> SEQ ID NO 39
<211> LENGTH: 50
<212> TYPE: DNA
<213> ORGANISM: Heterodera glycines

<400> SEQUENCE: 39
gctgctgagc atgtgttcgg ctgtgttttg tgtgcccccg gtagcttctc                50

<210> SEQ ID NO 40
<211> LENGTH: 50
<212> TYPE: DNA
<213> ORGANISM: Heterodera glycines

<400> SEQUENCE: 40
tctgtttcgt gcttctgctc tcatggatga caatgtgatg cacaaataca               50

<210> SEQ ID NO 41
<211> LENGTH: 63
<212> TYPE: DNA
<213> ORGANISM: Heterodera glycines
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t

<400> SEQUENCE: 41
ccaaaantgc ctccgaaccn acgacnattt tgttcagtat gatcaaggcg aagacccgat    60
gga                                                                  63

<210> SEQ ID NO 42
<211> LENGTH: 100
<212> TYPE: DNA
<213> ORGANISM: Heterodera glycines
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (70)..(70)
<223> OTHER INFORMATION: n is a, c, g, or t
<220> FEATURE:

<221> NAME/KEY: misc_feature
<222> LOCATION: (76)..(76)
<223> OTHER INFORMATION: n is a, c, g, or t

<400> SEQUENCE: 42
tctgtttcgt gcttctgctc tcatggatga caatgtgatg cacaaataca ccaaaantgc    60
ctccgaaccn acgacnattt tgttcagtat gatcaaggcg                          100

<210> SEQ ID NO 43
<211> LENGTH: 100
<212> TYPE: DNA
<213> ORGANISM: Heterodera glycines
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (70)..(70)
<223> OTHER INFORMATION: n is a, c, g, or t
<220> FEATURE:
<221> NAME/KEY: misc_feature
<222> LOCATION: (76)..(76)
<223> OTHER INFORMATION: n is a, c, g, or t

<400> SEQUENCE: 43
tctgtttcgt gcttctgctc tcatggatga caatgtgatg cacaaataca ccaaaantgc    60
ctccgaaccn acgacnattt tgttcagtat gatcaaggcg                          100

<210> SEQ ID NO 44
<211> LENGTH: 55
<212> TYPE: DNA
<213> ORGANISM: Heterodera glycines

<400> SEQUENCE: 44
tctgtttcgt gcttctgctc tcatggatga caatgtgatg cacaaataca ccaaa         55

<210> SEQ ID NO 45
<211> LENGTH: 389
<212> TYPE: DNA
<213> ORGANISM: Heterodera glycines
<220> FEATURE:
<221> NAME/KEY: misc_feature
<222> LOCATION: (248)..(248)
<223> OTHER INFORMATION: n is a, c, g, or t
<220> FEATURE:
<221> NAME/KEY: misc_feature
<222> LOCATION: (254)..(254)
<223> OTHER INFORMATION: n is a, c, g, or t
<220> FEATURE:
<221> NAME/KEY: misc_feature
<222> LOCATION: (286)..(286)
<223> OTHER INFORMATION: n is a, c, g, or t
<220> FEATURE:
<221> NAME/KEY: misc_feature
<222> LOCATION: (314)..(314)
<223> OTHER INFORMATION: n is a, c, g, or t
<220> FEATURE:
<221> NAME/KEY: misc_feature
<222> LOCATION: (353)..(383)
<223> OTHER INFORMATION: n is a, c, g, or t

<400> SEQUENCE: 45
ggatcctatc atgtccatgt tgaggtgacg aagcatcctt ccatcagacg ttgtactcga    60
tcggcaagtt cttgcggcgc accatcccgt ctccctggaa ccactcgagc ttgaacgtgg    120
tgtcggctgg gtccggtgtg ttggtccact ccgcggcggc ggcggcgccg ggcggttccg    180
gcacgttggt ccacgccacg gtcacacggt cgtccttggt gtcctcgctg ccggggtcga    240

-continued

```
aggcgtcnca gaanacggcc acgttgacag attcctttgg gccgancact ccgtccggcg    300
ggttcatgtt gatncgcttc ggtttggtgg tcttgaaggc ctgcagccat ggnnnnnnnn    360
nnnnnnnnnn nnnnnnnnnn nnngaattc                                      389
```

US 7,803,984 B2

COMPOSITIONS AND METHODS FOR CONTROLLING PLANT PARASITIC NEMATODES

This application claims the benefit of U.S. Provisional Application 60/395,153, filed Jul. 10, 2002.

This invention was made with government support under Hatch Grant No. KS699 awarded by CRSEES. The Government has certain rights in the invention.

FIELD OF THE INVENTION

The present invention relates to compositions and methods for controlling nematode infestation of plants or animals. In particular, the present invention provides vectors comprising sequences designed to control nematodes by RNA interference (RNAi) and transgenic plants transformed with such vectors.

BACKGROUND OF THE INVENTION

The soybean cyst nematode (SCN), *Heterodera glycines*, is the primary biotic factor limiting soybean production in the United States, accounting for 40% of total disease losses (Wrather, J. A., Anderson, T. R., Arsyad, D. M., Gai, J., Ploper, L. D., Porta-Puglia, A., Ram, H. H., Yorinori, J. T. 1997. Soybean disease loss estimates for the top 10 soybean producing countries in 1994. Plant Disease 81:107-110). The nematode is a relatively recent introduction to Kansas (Sim, T., I V., and Todd, T. C. 1986. First field observation of the soybean cyst nematode in Kansas. Plant Disease 70:603), yet it's present distribution encompasses 40 counties across six of the nine state districts. Based on the results of an extensive grower sampling program (SCN Coalition), approximately 10% of the state's soybean production fields are estimated to be infested with *H. glycines*, with nematode prevalence in several areas exceeding 40%. Yield losses in individual infested fields in Kansas range from 10% to 40%, depending on environment (Todd, T. C., Schapaugh, W. T., Long, J. H., and Holmes, B. 1995. Field response of soybean in maturity groups III-V to *Heterodera glycines* in Kansas. Supplement to the Journal of Nematology 27:628-633.).

Nonhost crops and resistant varieties are the most widely used management strategies for SCN. Both effectively reduce nematode population densities, but declines in the North Central region are relatively slow and elimination unlikely. Resistance, while readily available for the most common variants (races) of SCN, has a narrow genetic base (~85% of resistant varieties derive their resistance from a single source), and is limited or unavailable for some populations. In addition, adaptation of nematode populations to resistant varieties poses a significant threat to the long-term management of this pest (Holmes, B. A., Todd, T. C., and Schapaugh, W. T. 1999. Effect of resistance source on SCN populations. National Soybean Cyst Nematode Conference, Orlando, Fla., Jan. 7-8, 1999; Young, L. D. 1998. Managing soybean resistance to *Heterodera glycines*. Supplement to the Journal of Nematology 30:525-529).

Novel approaches to SCN management are needed to complement current strategies, and prolong the effectiveness of available resistance genes.

SUMMARY OF THE INVENTION

The present invention relates to compositions and methods for controlling nematode infestation of plants or animals. In particular, the present invention provides vectors comprising sequences designed to control nematodes by RNA interference (RNAi) and transgenic plants transformed with such vectors.

Accordingly, in some embodiments, the present invention provides transgenic plants comprising heterologous nucleic acid sequences encoding a double stranded nematode RNA sequence, wherein said double stranded RNA sequence inhibits the proliferation of nematodes ingesting said double stranded nematode RNA sequence. The present invention is not limited to any particular expression construct or construct design. Indeed, the use of a variety of constructs and designs are contemplated. In some embodiments, the heterologous nucleic acid sequences are operably linked to the same promoter. In other embodiments, the heterologous nucleic acid sequences are operably linked to separate or different promoter sequences. In still other embodiments, the heterologous nucleic acid sequences are separated by a loop sequence. In some embodiments, the promoter is a tissue specific promoter, while in other embodiments the promoter is a constitutive promoter. The present invention is not limited to the use of any particular heterologous nucleic acid sequence. Indeed, the use of a variety of sequences is contemplated, including, but not limited to those that complementary to an RNA sequence selected from the group consisting of nematode Major sperm protein, RNA polymerase II, and Chitin synthase RNA sequences. In other embodiments, the sequences are selected from Tables 1 or 2, supra. Likewise, the present invention is not limited to heterologous nucleic acid sequences of any particular length. Indeed, heterologous nucleic acid sequences of varying lengths may be utilized, including those from about 21 bases in length to the full length of the target RNA. In still further embodiments, the present invention provides plant tissue or material from the foregoing transgenic plants. The present invention is not limited to any particular tissue or material. Indeed, a variety of plant tissues and materials are contemplated. Accordingly, in some embodiments, the present invention provides seeds, leaves, roots, or processed materials derived from the foregoing transgenic plants.

In some embodiments, the present invention provides vectors comprising heterologous nucleic acid sequences encoding a double stranded nematode RNA sequence, wherein said double stranded RNA sequence inhibits the proliferation of nematodes ingesting said double stranded RNA sequence. The present invention is not limited to any particular vector or vector design. Indeed, the use of a variety of vectors and designs are contemplated. In some embodiments, the heterologous nucleic acid sequences are operably linked to the same promoter. In other embodiments, the heterologous nucleic acid sequences are operably linked to separate or different promoter sequences. In still other embodiments, the heterologous nucleic acid sequences are separated by a loop sequence. In some embodiments, the promoter is a tissue specific promoter, while in other embodiments the promoter is a constitutive promoter. The present invention is not limited to the use of any particular heterologous nucleic acid sequence. Indeed, the use of a variety of sequences is contemplated, including, but not limited to those that complementary to an RNA sequence selected from the group consisting of nematode Major sperm protein, RNA polymerase II, and Chitin synthase RNA sequences. In some embodiments, the double stranded nematode RNA is complementary to an embryonic lethal phenotype gene. In further embodiments, the double stranded nematode RNA is complementary to a sterile phenotype gene. In other embodiments, the sequences are selected from Tables 1 or 2, supra. Likewise, the present invention is not limited to heterologous nucleic acid sequences of any particular length. Indeed, heterologous nucleic acid sequences of varying lengths may be utilized, including those from about 21 bases in length to the full length of the target RNA. In still further embodiments, the present invention provides a transgenic plant comprising the foregoing vectors. In other embodiments, the present invention provides animal feeds comprising plant tissue from the foregoing transgenic plants. In some embodiments, the plant tissue is selected from seeds and leaves. In still further embodiments, the present invention provides pharmaceutical compositions comprising materials derived from the foregoing transgenic plants.

In still further embodiments, the present invention provides methods of creating transgenic plants comprising transfecting a plant or plant tissue with the foregoing vector. In other embodiments, the present invention provides the transgenic plant produced by this process. In some embodiments, the methods further comprises harvesting the transgenic material and using the transgenic plant material to produce a pharmaceutical composition or animal feed. The present invention also provides the pharmaceutical compositions and animal feeds produced by these processes.

In still other embodiments, the present invention provides methods for controlling nematodes comprising: a) providing transgenic plant tissue comprising heterologous DNA sequences encoding a double stranded nematode RNA; and b) growing said transgenic plant so that said double stranded nematode RNA is expressed in plant tissue; wherein the proliferation of nematodes feeding on said plant tissue is reduced as compared to nematodes feeding on non-transgenic plant tissue. The present invention is not limited to inhibiting the proliferation of any particular type of nematodes. Indeed, the inhibition of proliferation of a number of different types of nematodes is contemplated, including, but not limited to plant parasitic nematodes and animal parasitic nematodes. In some preferred embodiments, the double stranded nematode RNA is orally active to prevent the proliferation of nematodes. Accordingly, in some embodiment the nematodes orally ingest said double stranded nematode RNA. The present invention is not limited to the use of any particular expression vector or vector design. Indeed, the use of a variety of vectors and designs are contemplated. In some embodiments, the heterologous nucleic acid sequences are operably linked to the same promoter. In other embodiments, the heterologous nucleic acid sequences are operably linked to separate or different promoter sequences. In still other embodiments, the heterologous nucleic acid sequences are separated by a loop sequence. In some embodiments, the promoter is a tissue specific promoter, while in other embodiments the promoter is a constitutive promoter. The present invention is not limited to the use of any particular heterologous nucleic acid sequence. Indeed, the use of a variety of sequences is contemplated, including, but not limited to those that complementary to an RNA sequence selected from the group consisting of nematode Major sperm protein, RNA polymerase II, and Chitin synthase RNA sequences. In some embodiments, the double stranded nematode RNA is complementary to an embryonic lethal phenotype gene. In further embodiments, the double stranded nematode RNA is complementary to a sterile phenotype gene. In other embodiments, the sequences are selected from Tables 1 or 2, supra. Likewise, the present invention is not limited to heterologous nucleic acid sequences of any particular length. Indeed, heterologous nucleic acid sequences of varying lengths may be utilized, including those from about 21 bases in length to the full length of the target RNA. In some embodiments, the double stranded nematode RNA is complementary to an embryonic lethal phenotype gene. In further embodiments, the double stranded nematode RNA is complementary to a sterile phenotype gene. In still further embodiments, the nematodes feeding on said plant tissue are killed.

In some embodiments, the present invention provides a transgenic plant expressing a heterologous double stranded nematode RNA sequence at a level such that nematodes ingesting said heterologous double stranded nematode RNA sequences exhibit decreased proliferation as compared to nematodes feeding on non-transgenic plants.

In still further embodiments, the present invention provides pharmaceutical compositions comprising plant material derived from the foregoing transgenic plants.

In some embodiments, the present invention provides for the use of transgenic plant material comprising a double stranded nematode RNA sequence to inhibit the proliferation of parasitic nematodes in an animal or plant host.

In still further embodiments, the present invention provides compositions according to the claims as substantially described in the application herein with reference to the figures and/or the specification.

DESCRIPTION OF THE FIGURES

FIG. 1 is the sequence for *H. glycines* Major sperm protein (SEQ ID NO:1).

FIG. 2A is a subsequence of *H. glycines* Major sperm protein (SEQ ID NO:4).

FIG. 2B is a subsequence of *H. glycines* Major sperm protein (SEQ ID NO:45).

FIG. 3 is the reverse complement (SEQ ID NO:5) of SEQ ID NO:4.

FIG. 4 is the assembled MSPi sequence (SEQ ID NO:6).

FIG. 5 is the sequence for *H. glycines* RNA polymerase II (SEQ ID NO:9).

FIG. 6 provides a 279 base pair exon (SEQ ID NO:10) from the RNA polymerase II gene of *H. glycines*.

FIG. 7 is a 285 bp sequence (SEQ ID NO:13) prepared from SEQ ID NO:10.

FIG. 8 is the reverse complement (SEQ ID NO:14) of SEQ ID NO:13.

FIG. 10 provides the sense sequence (SEQ ID NO:17) used in the RNA polymerase II RNAi construct.

FIG. 12 provides the sequence for *H. glycines* Chitin synthase.

FIG. 13 provides a graph of soybean cyst production on transgenic lines vs. control plants as functional of cysts per plant.

FIG. 14 provides a graph of soybean cyst production on transgenic lines vs. control plants as functional of cysts per gram of root tissue. "*" indicates data is significant.

FIG. 15 provides a graph of soybean cyst nematode egg production on transgenic lines vs. control plants as an average number of eggs per plant. "*" indicates data is significant.

FIG. 16 provides a graph of soybean cyst nematode egg production on transgenic lines vs. control plants as an average number of eggs per gram of root. "*" indicates data is significant.

FIG. 17 provides a graph of soybean cyst nematode egg production on transgenic lines vs. control plants as an average number of eggs per cyst.

DEFINITIONS

Figure 9:
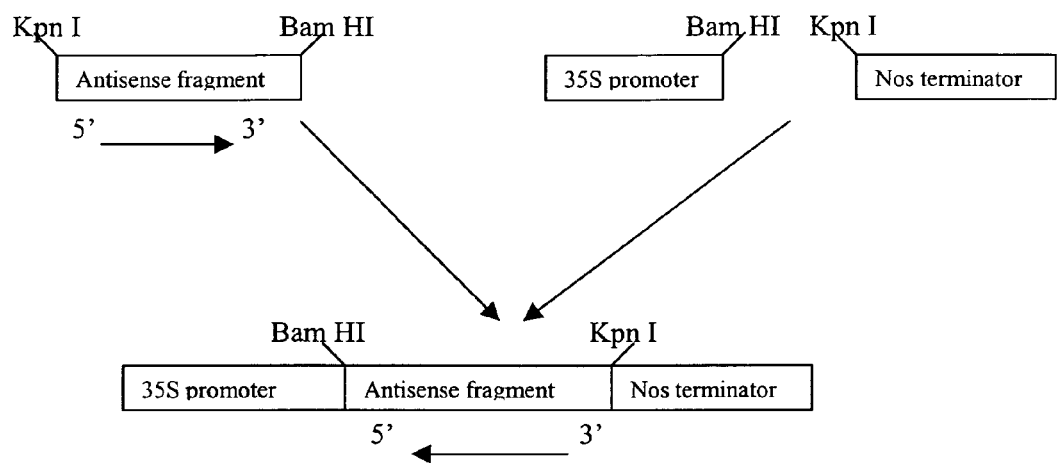
FIG. 9 provides a pictorial representation of the cloning strategy for the RNA polymerase II RNAi construct.

To facilitate an understanding of the present invention, a number of terms and phrases as used herein are defined below:

The term "plant" is used in it broadest sense. It includes, but is not limited to, any species of woody, ornamental or decorative, crop or cereal, fruit or vegetable plant, and photosynthetic green algae (e.g., *Chlamydomonas reinhardtii*). It also refers to a plurality of plant cells that are largely differentiated into a structure that is present at any stage of a plant's development. Such structures include, but are not limited to, a fruit, shoot, stem, leaf, flower petal, etc. The term "plant tissue" includes differentiated and undifferentiated tissues of plants including those present in roots, shoots, leaves, pollen, seeds and tumors, as well as cells in culture (e.g., single cells, protoplasts, embryos, callus, etc.). Plant tissue may be in planta, in organ culture, tissue culture, or cell culture. The term "plant part" as used herein refers to a plant structure, a plant organ, or a plant tissue.

The term "crop" or "crop plant" is used in its broadest sense. The term includes, but is not limited to, any species of plant or algae edible by humans or used as a feed for animals or used, or consumed by humans, or any plant or algae used in industry or commerce.

The term plant cell "compartments or organelles" is used in its broadest sense. The term includes but is not limited to, the endoplasmic reticulum, Golgi apparatus, trans Golgi network, plastids including chloroplasts, proplastids, and leucoplasts, sarcoplasmic reticulum, glyoxysomes, mitochondrial, chloroplast, and nuclear membranes, and the like.

As used herein, the term "Major sperm protein (MSP)" when used in reference to a protein or nucleic acid refers to a protein or nucleic acid encoding a protein that shares greater than about 50% identity with any of SEQ ID NOS: 1, 4-6, and 25-30. Thus, the term MSP encompasses both proteins that are identical to wild-type MSP and those that are derived from wild type MSP protein (e.g., variants of MSP).

As used herein, the terms "Major sperm protein gene" and "Major sperm protein nucleic acid sequence" refer to the full length *H. glycines* Major sperm protein sequence, as well as sequence provided as SEQ ID NOS: 1, 4-6, and 25-30, sequences which bind to SEQ ID NOS: 1, 4-6, and 25-30 under conditions of high stringency, and nematode Major sperm protein sequences available in public databases. These terms encompass fragments of the MSP sequences and include DNA, cDNA, and RNA (e.g., mRNA) sequences.

As used herein, the term "RNA polymerase II" when used in reference to a protein or nucleic acid refers to a protein or nucleic acid encoding a protein that shares greater than about 50% identity with any of SEQ ID NOS: 9, 10, 13, 14, 17 and 31-37. Thus, the term RNA polymerase II encompasses both proteins that are identical to wild-type RNA polymerase II and those that are derived from wild type RNA polymerase II protein (e.g., variants of RNA polymerase II).

As used herein, the terms "RNA polymerase II gene" and "RNA polymerase II nucleic acid sequence" refer to the full length *H. glycines* RNA polymerase II protein sequence, as well as sequence provided as SEQ ID NOS: SEQ ID NOS: 9, 10, 13, 14, 17 and 31-37, sequences which bind to SEQ ID NOS: SEQ ID NOS: 9, 10, 13, 14, 17 and 31-37 under conditions of high stringency, and nematode RNA polymerase II sequences available in public databases. These terms encompass fragments of the RNA polymerase II sequences and include DNA, cDNA, and RNA (e.g., mRNA) sequences.

As used herein, the term "Chitin synthase" when used in reference to a protein or nucleic acid refers to a protein or nucleic acid encoding a protein that shares greater than about 50% identity with any of SEQ ID NOS: 18 and 38-44. Thus, the term Chitin synthase encompasses both proteins that are identical to wild-type Chitin synthase and those that are derived from wild type Chitin synthase protein (e.g., variants of Chitin synthase).

As used herein, the terms "Chitin synthase gene" and "Chitin synthase nucleic acid sequence" refer to the full length *H. glycines* Chitin synthase protein sequence, as well as sequence provided as SEQ ID NOS: 18 and 38-44, sequences which bind to SEQ ID NOs: SEQ ID NOS: 18 and 38-44 under conditions of high stringency, and nematode Chitin synthase sequences available in public databases. These terms encompass fragments of the Chitin synthase sequences and include DNA, cDNA, and RNA (e.g., mRNA) sequences.

The term "host cell" refers to any cell capable of replicating and/or transcribing and/or translating a heterologous gene.

The term "heterologous," when used in reference to DNA sequences or genes, means a DNA sequence encoding a protein, polypeptide, RNA, or a portion of any thereof, whose exact amino acid sequence is not normally found in the host cell, but is introduced by standard gene transfer techniques.

The term "nematode" as used herein refers to worms that are members of the phylum Nemata.

The term "RNA interference" or "RNAi" refers to the silencing or decreasing of gene expression by iRNA or siRNAs. It is the process of sequence-specific, post-transcriptional gene silencing in animals and plants, initiated by iRNA that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the function of the target RNA may be complete or partial.

The term "interfering RNA (iRNA)" refers to a double stranded RNA molecule that mediates RNA interference (RNAi). At least one strand of the duplex or double-stranded region of an iRNA is substantially homologous to or substantially complementary to a target RNA molecule. The strand complementary to a target RNA molecule is the "antisense strand;" the strand homologous to the target RNA molecule is the "sense strand," and is also complementary to the iRNA antisense strand. iRNAs may also contain additional sequences; non-limiting examples of such sequences include linking sequences, or loops, as well as stem and other folded structures.

The iRNA can serve as a source of siRNA. siRNAs generally comprise a duplex, or double-stranded region, of about 18-25 nucleotides long; often siRNAs contain from about two to four unpaired nucleotides at the 3' end of each strand. At least one strand of the duplex or double-stranded region of a siRNA is substantially homologous to or substantially complementary to a target RNA molecule. The strand complementary to a target RNA molecule is the "antisense strand;" the strand homologous to the target RNA molecule is the "sense strand," and is also complementary to the siRNA antisense strand. siRNAs may also contain additional sequences; non-limiting examples of such sequences include linking sequences, or loops, as well as stem and other folded structures. siRNAs appear to function as key intermediaries in triggering RNA interference in invertebrates and in vertebrates, and in triggering sequence-specific RNA degradation during post-transcriptional gene silencing in plants.

The term "target RNA molecule" refers to an RNA molecule to which at least one strand of the short double-stranded region of an iRNA is homologous or complementary. Typically, when such homology or complementary is about 100%, the siRNA is able to silence or inhibit expression of the target RNA molecule. Although it is believed that processed mRNA is a target of siRNA, the present invention is not limited to any particular hypothesis, and such hypotheses are not necessary to practice the present invention. Thus, it is contemplated that other RNA molecules may also be targets of siRNA. Such targets include unprocessed mRNA, ribosomal RNA, and viral RNA genomes.

As used herein, the term "loop sequence" refers to a nucleic acid sequence that is placed between two nucleic sequences that are complementary to each other and which forms a loops when the complementary nucleic acid sequences hybridize to one another.

The term "nematode target RNA" as used herein refers to an RNA that is expressed in a nematode.

The term "double stranded nematode RNA sequence" refers to an iRNA that is specific for a nematode target RNA.

The term "inhibits the proliferation of nematodes" refers to a reduction in nematode parasitism of a host organism. The inhibition of proliferation can be mediated in a variety of ways, including, but not limited to, decreasing the fitness of the nematode by decreasing or inhibiting the expression of genes required for nematode fitness (e.g., RNA polymerase II) or inhibiting genes required for reproduction (e.g., Major sperm protein or Chitin synthase). A variety of assays may be used to measure proliferation, including, but not limited to measuring the number of roots cysts that develop in plants exposed to nematodes.

As used herein, the term "orally active to prevent the proliferation of nematodes" refers to a double stranded nematode RNA sequence that inhibits the proliferation of nematodes when orally ingested by the nematodes.

The terms "protein" and "polypeptide" refer to compounds comprising amino acids joined via peptide bonds and are used interchangeably.

As used herein, "amino acid sequence" refers to an amino acid sequence of a protein molecule. "Amino acid sequence" and like terms, such as "polypeptide" or "protein," are not meant to limit the amino acid sequence to the complete, native amino acid sequence associated with the recited protein molecule. Furthermore, an "amino acid sequence" can be deduced from the nucleic acid sequence encoding the protein.

The term "portion" when used in reference to a protein (as in "a portion of a given protein") refers to fragments of that protein. The fragments may range in size from four amino acid residues to the entire amino sequence minus one amino acid.

The term "homology" when used in relation to amino acids refers to a degree of similarity or identity. There may be partial homology or complete homology (i.e., identity). "Sequence identity" refers to a measure of relatedness between two or more proteins, and is given as a percentage with reference to the total comparison length. The identity calculation takes into account those amino acid residues that are identical and in the same relative positions in their respective larger sequences. Calculations of identity may be performed by algorithms contained within computer programs.

The term "homolog" or "homologous" when used in reference to a polypeptide refers to a high degree of sequence identity between two polypeptides, or to a high degree of similarity between the three-dimensional structure or to a high degree of similarity between the active site and the mechanism of action. In a preferred embodiment, a homolog has a greater than 60% sequence identity, and more preferable greater than 75% sequence identity, and still more preferably greater than 90% sequence identity, with a reference sequence.

The terms "variant" and "mutant" when used in reference to a polypeptide refer to an amino acid sequence that differs by one or more amino acids from another, usually related polypeptide. The variant may have "conservative" changes, wherein a substituted amino acid has similar structural or chemical properties (e.g., replacement of leucine with isoleucine). More rarely, a variant may have "non-conservative" changes (e.g., replacement of a glycine with a tryptophan). Similar minor variations may also include amino acid deletions or insertions (in other words, additions), or both. Guidance in determining which and how many amino acid residues may be substituted, inserted or deleted without abolishing biological activity may be found using computer programs well known in the art, for example, DNAStar software. Variants can be tested in functional assays. Preferred variants have less than 10%, and preferably less than 5%, and still more preferably less than 2% changes (whether substitutions, deletions, and so on).

The term "gene" refers to a nucleic acid (e.g., DNA or RNA) sequence that comprises coding sequences necessary for the production of an RNA, or a polypeptide or its precursor (e.g., proinsulin). A functional polypeptide can be encoded by a full length coding sequence or by any portion of the coding sequence as long as the desired activity or functional properties (e.g., enzymatic activity, ligand binding, signal transduction, etc.) of the polypeptide are retained. The term "portion" when used in reference to a gene refers to fragments of that gene. The fragments may range in size from a few nucleotides to the entire gene sequence minus one nucleotide. Thus, "a nucleotide comprising at least a portion of a gene" may comprise fragments of the gene or the entire gene.

The term "gene" also encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "heterologous gene" refers to a gene encoding a factor that is not in its natural environment (i.e., has been altered by the hand of man). For example, a heterologous gene includes a gene from one species introduced into another species. A heterologous gene also includes a gene native to an organism that has been altered in some way (e.g., mutated, added in multiple copies, linked to a non-native promoter or enhancer sequence, etc.). Heterologous genes may comprise plant gene sequences that comprise cDNA forms of a plant gene; the cDNA sequences may be expressed in either a sense (to produce mRNA) or anti-sense orientation (to produce an anti-sense RNA transcript that is complementary to the mRNA transcript). Heterologous genes are distinguished from endogenous plant genes in that the heterologous gene sequences are typically joined to nucleotide sequences comprising regulatory elements such as promoters that are not found naturally associated with the gene for the protein encoded by the heterologous gene or with plant gene sequences in the chromosome, or are associated with portions of the chromosome not found in nature (e.g., genes expressed in loci where the gene is not normally expressed).

The term "oligonucleotide" refers to a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof.

The term "an oligonucleotide having a nucleotide sequence encoding a gene" or "a nucleic acid sequence encoding" a specified polypeptide refers to a nucleic acid sequence comprising the coding region of a gene or in other words the nucleic acid sequence which encodes a gene product. The coding region may be present in either a cDNA, genomic DNA or RNA form. When present in a DNA form, the oligonucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

The terms "complementary" and "complementarity" refer to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

The term "homology" when used in relation to nucleic acids refers to a degree of complementarity. There may be partial homology or complete homology (i.e., identity). "Sequence identity" refers to a measure of relatedness between two or more nucleic acids, and is given as a percentage with reference to the total comparison length. The identity calculation takes into account those nucleotide residues that are identical and in the same relative positions in their respective larger sequences. Calculations of identity may be performed by algorithms contained within computer programs such as "GAP" (Genetics Computer Group, Madison, Wis.) and "ALIGN" (DNAStar, Madison, Wis.). A partially complementary sequence is one that at least partially inhibits (or competes with) a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a sequence that is completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

When used in reference to a double-stranded nucleic acid sequence such as a cDNA or genomic clone, the term "substantially homologous" refers to any probe which can hybridize to either or both strands of the double-stranded nucleic acid sequence under conditions of low stringency as described infra.

The term "hybridization" refers to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

The term "$T_m$" refers to the "melting temperature" of a nucleic acid. The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m = 81.5 + 0.41(\% \text{ G+C})$, when a nucleic acid is in aqueous solution at 1 M NaCl (See e.g., Anderson and Young, Quantitative Filter Hybridization (1985) *in Nucleic Acid Hybridization*). Other references include more sophisticated computations that take structural as well as sequence characteristics into account for the calculation of $T_m$.

As used herein the term "stringency" refers to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "low" stringency are often required with nucleic acids that are derived from organisms that are genetically diverse, as the frequency of complementary sequences is usually less.

"High stringency conditions" when used in reference to nucleic acid hybridization comprise conditions equivalent to binding or hybridization at 42° C. in a solution consisting of 5×SSPE (43.8 g/l NaCl, 6.9 g/l NaH$_2$PO$_4$ H$_2$O and 1.85 g/l EDTA, pH adjusted to 7.4 with NaOH), 0.5% SDS, 5×Denhardt's reagent and 100 µg/ml denatured salmon sperm DNA followed by washing in a solution comprising 0.1×SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l NaH$_2$PO$_4$ H$_2$O and 1.85 g/l EDTA, pH adjusted to 7.4 with NaOH), 0.5% SDS, 5×Denhardt's reagent and 100 µg/ml denatured salmon sperm DNA followed by washing in a solution comprising 1.0×SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l NaH$_2$PO$_4$ H$_2$O and 1.85 g/l EDTA, pH adjusted to 7.4 with NaOH), 0.1% SDS, 5×Denhardt's reagent [50×Denhardt's contains per 500 ml: 5 g Ficoll (Type 400, Pharamcia), 5 g BSA (Fraction V; Sigma)] and 100 µg/ml denatured salmon sperm DNA followed by washing in a solution comprising 5×SSPE, 0.1% SDS at 42° C. when a probe of about 500 nucleotides in length is employed.

It is well known that numerous equivalent conditions may be employed to comprise desired stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

When used in reference to a double-stranded nucleic acid sequence such as a cDNA or genomic clone, the term "substantially homologous" refers to any probe that can hybridize to either or both strands of the double-stranded nucleic acid sequence under conditions of low to high stringency as described above.

When used in reference to a single-stranded nucleic acid sequence, the term "substantially homologous" refers to any probe that can hybridize (i.e., it is the complement of) the single-stranded nucleic acid sequence under conditions of low to high stringency as described above.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Q βreplicase, MDV-1 RNA is the specific template for the replicase (Kacian et al. (1972) Proc. Natl. Acad. Sci. USA, 69:3038). Other nucleic acid will not be replicated by this amplification enzyme. Similarly, in the case of T7 RNA polymerase, this amplification enzyme has a stringent specificity for its own promoters (Chamberlin et al. (1970) Nature, 228:227). In the case of T4 DNA ligase, the enzyme will not ligate the two oligonucleotides or polynucleotides, where there is a mismatch between the oligonucleotide or polynucleotide substrate and the template at the ligation junction (Wu and Wallace (1989) Genomics, 4:560). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.) (1989) *PCR Technology*, Stockton Press).

The term "amplifiable nucleic acid" refers to nucleic acids that may be amplified by any amplification method. It is contemplated that "amplifiable nucleic acid" will usually comprise "sample template."

The term "sample template" refers to nucleic acid originating from a sample that is analyzed for the presence of "target" (defined below). In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

The term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

The term "polymerase chain reaction" ("PCR") refers to the method of K. B. Mullis U.S. Pat. Nos. 4,683,195, 4,683, 202, and 4,965,188, that describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

The terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

The term "amplification reagents" refers to those reagents (deoxyribonucleotide triphosphates, buffer, etc.), needed for amplification except for primers, nucleic acid template, and the amplification enzyme. Typically, amplification reagents along with other reaction components are placed and contained in a reaction vessel (test tube, microwell, etc.).

The term "reverse-transcriptase" or "RT-PCR" refers to a type of PCR where the starting material is mRNA. The starting mRNA is enzymatically converted to complementary DNA or "cDNA" using a reverse transcriptase enzyme. The cDNA is then used as a "template" for a "PCR" reaction.

The term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and into protein, through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

The terms "in operable combination", "in operable order" and "operably linked" refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "regulatory element" refers to a genetic element that controls some aspect of the expression of nucleic acid sequences. For example, a promoter is a regulatory element that facilitates the initiation of transcription of an operably linked coding region. Other regulatory elements are splicing signals, polyadenylation signals, termination signals, etc.

Transcriptional control signals in eukaryotes comprise "promoter" and "enhancer" elements. Promoters and enhancers consist of short arrays of DNA sequences that interact specifically with cellular proteins involved in transcription (Maniatis, et al., Science 236:1237, 1987). Promoter and enhancer elements have been isolated from a variety of eukaryotic sources including genes in yeast, insect, mammalian and plant cells. Promoter and enhancer elements have also been isolated from viruses and analogous control elements, such as promoters, are also found in prokaryotes. The selection of a particular promoter and enhancer depends on the cell type used to express the protein of interest. Some eukaryotic promoters and enhancers have a broad host range while others are functional in a limited subset of cell types (for review, see Voss, et al., Trends Biochem. Sci., 11:287, 1986; and Maniatis, et al., supra 1987).

The terms "promoter element," "promoter," or "promoter sequence" as used herein, refer to a DNA sequence that is located at the 5' end (i.e. precedes) the protein coding region of a DNA polymer. The location of most promoters known in nature precedes the transcribed region. The promoter functions as a switch, activating the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA.

Promoters may be tissue specific or cell specific. The term "tissue specific" as it applies to a promoter refers to a promoter that is capable of directing selective expression of a nucleotide sequence of interest to a specific type of tissue (e.g., seed tissue) in the relative absence of expression of the same nucleotide sequence of interest in a different type of tissue (e.g., leave tissue). Tissue specificity of a promoter may be evaluated by, for example, operably linking a reporter gene to the promoter sequence to generate a reporter construct, introducing the reporter construct into the genome of a plant such that the reporter construct is integrated into every tissue of the resulting transgenic plant, and detecting the expression of the reporter gene (e.g., detecting mRNA, protein, or the activity of a protein encoded by the reporter gene) in different tissues of the transgenic plant. The detection of a greater level of expression of the reporter gene in one or more tissues relative to the level of expression of the reporter gene in other tissues shows that the promoter is specific for the tissues in which greater levels of expression are detected. The term "cell type specific" as applied to a promoter refers to a promoter which is capable of directing selective expression of a nucleotide sequence of interest in a specific type of cell in the relative absence of expression of the same nucleotide sequence of interest in a different type of cell within the same tissue. The term "cell type specific" when applied to a promoter also means a promoter capable of promoting selective expression of a nucleotide sequence of interest in a region within a single tissue. Cell type specificity of a promoter may be assessed using methods well known in the art, e.g., immunohistochemical staining. Briefly, tissue sections are embedded in paraffin, and paraffin sections are reacted with a primary antibody that is specific for the polypeptide product encoded by the nucleotide sequence of interest whose expression is controlled by the promoter. A labeled (e.g., peroxidase conjugated) secondary antibody that is specific for the primary antibody is allowed to bind to the sectioned tissue and specific binding detected (e.g., with avidin/biotin) by microscopy.

Promoters may be constitutive or regulatable. The term "constitutive" when made in reference to a promoter means that the promoter is capable of directing transcription of an operably linked nucleic acid sequence in the absence of a stimulus (e.g., heat shock, chemicals, light, etc.). Typically, constitutive promoters are capable of directing expression of a transgene in substantially any cell and any tissue. Exemplary constitutive plant promoters include, but are not limited to SD Cauliflower Mosaic Virus (CaMV SD; see e.g., U.S. Pat. No. 5,352,605, incorporated herein by reference), mannopine synthase, octopine synthase (ocs), superpromoter (see e.g., WO 95/14098), and ubi3 (see e.g., Garbarino and Belknap (1994) Plant Mol. Biol. 24:119-127) promoters. Such promoters have been used successfully to direct the expression of heterologous nucleic acid sequences in transformed plant tissue.

In contrast, a "regulatable" promoter is one which is capable of directing a level of transcription of an operably linked nuclei acid sequence in the presence of a stimulus (e.g., heat shock, chemicals, light, etc.) which is different from the level of transcription of the operably linked nucleic acid sequence in the absence of the stimulus.

The enhancer and/or promoter may be "endogenous" or "exogenous" or "heterologous." An "endogenous" enhancer or promoter is one that is naturally linked with a given gene in the genome. An "exogenous" or "heterologous" enhancer or promoter is one that is placed in juxtaposition to a gene by means of genetic manipulation (i.e., molecular biological techniques) such that transcription of the gene is directed by the linked enhancer or promoter. For example, an endogenous promoter in operable combination with a first gene can be isolated, removed, and placed in operable combination with a second gene, thereby making it a "heterologous promoter" in operable combination with the second gene. A variety of such combinations are contemplated (e.g., the first and second genes can be from the same species, or from different species.

The presence of "splicing signals" on an expression vector often results in higher levels of expression of the recombinant transcript in eukaryotic host cells. Splicing signals mediate the removal of introns from the primary RNA transcript and consist of a splice donor and acceptor site (Sambrook, et al. (1989) *Molecular Cloning: A Laboratory Manual*, 2nd ed., Cold Spring Harbor Laboratory Press, New York, pp. 16.7-16.8). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly(A) site" or "poly(A) sequence" as used herein denotes a DNA sequence which directs both the termination and polyadenylation of the nascent RNA transcript. Efficient polyadenylation of the recombinant transcript is desirable, as transcripts lacking a poly(A) tail are unstable and are rapidly degraded. The poly (A) signal utilized in an expression vector may be "heterologous" or "endogenous." An endogenous poly(A) signal is one that is found naturally at the 3' end of the coding region of a given gene in the genome. A heterologous poly(A) signal is one which has been isolated from one gene and positioned 3' to another gene. A commonly used heterologous poly(A) signal is the SV40 poly(A) signal. The SV40 poly(A) signal is contained on a 237 bp BamHI/BclI restriction fragment and directs both termination and polyadenylation (Sambrook, supra, at 16.6-16.7).

The term "selectable marker" refers to a gene which encodes an enzyme having an activity that confers resistance to an antibiotic or drug upon the cell in which the selectable marker is expressed, or which confers expression of a trait which can be detected (e.g., luminescence or fluorescence). Selectable markers may be "positive" or "negative." Examples of positive selectable markers include the neomycin phosphotransferase (NPTII) gene which confers resistance to G418 and to kanamycin, and the bacterial hygromycin phosphotransferase gene (hyg), which confers resistance to the antibiotic hygromycin. Negative selectable markers encode an enzymatic activity whose expression is cytotoxic to the cell when grown in an appropriate selective medium. For example, the HSV-tk gene is commonly used as a negative selectable marker. Expression of the HSV-tk gene in cells grown in the presence of gancyclovir or acyclovir is cytotoxic; thus, growth of cells in selective medium containing gancyclovir or acyclovir selects against cells capable of expressing a functional HSV TK enzyme.

The term "vector refers to nucleic acid molecules that transfer DNA segment(s) from one cell to another. The term "vehicle" is sometimes used interchangeably with "vector."

The terms "expression vector" or "expression cassette" refer to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "transfection", "transformation", "transfected" and "transformed" are used interchangeably and refer to the introduction of foreign DNA into cells. Transfection may be accomplished by a variety of means known to the art including calcium phosphate-DNA co-precipitation, DEAE-dextran-mediated transfection, polybrene-mediated transfection, glass beads, electroporation, microinjection, liposome fusion, lipofection, protoplast fusion, viral infection, biolistics (i.e., particle bombardment) and the like.

The terms "infecting" and "infection" when used with a bacterium refer to co-incubation of a target biological sample, (e.g., cell, tissue, etc.) with the bacterium under conditions such that nucleic acid sequences contained within the bacterium are introduced into one or more cells of the target biological sample.

The term "Agrobacterium" refers to a soil-borne, Gram-negative, rod-shaped phytopathogenic bacterium which causes crown gall. The term "Agrobacterium" includes, but is not limited to, the strains *Agrobacterium tumefaciens*, (which typically causes crown gall in infected plants), and *Agrobacterium rhizogens* (which causes hairy root disease in infected host plants). Infection of a plant cell with Agrobacterium generally results in the production of opines (e.g., nopaline, agropine, octopine etc.) by the infected cell. Thus, Agrobacterium strains which cause production of nopaline (e.g., strain LBA4301, C58, A208, GV3101) are referred to as "nopaline-type" Agrobacteria; Agrobacterium strains which cause production of octopine (e.g., strain LBA4404, Ach5, B6) are referred to as "octopine-type" Agrobacteria; and Agrobacterium strains which cause production of agropine (e.g., strain EHA105, EHA101, A281) are referred to as "agropine-type" Agrobacteria.

The terms "bombarding, "bombardment," and "biolistic bombardment" refer to the process of accelerating particles towards a target biological sample (e.g., cell, tissue, etc.) to effect wounding of the cell membrane of a cell in the target biological sample and/or entry of the particles into the target biological sample. Methods for biolistic bombardment are known in the art (e.g., U.S. Pat. No. 5,584,807, the contents of which are incorporated herein by reference), and are commercially available (e.g., the helium gas-driven microprojectile accelerator (PDS-1000/He, BioRad).

The term "microwounding" when made in reference to plant tissue refers to the introduction of microscopic wounds in that tissue. Microwounding may be achieved by, for example, particle bombardment as described herein.

The term "transgenic" when used in reference to a plant or fruit or seed (i.e., a "transgenic plant" or "transgenic fruit" or a "transgenic seed") refers to a plant or fruit or seed that contains at least one heterologous gene in one or more of its cells. The term "transgenic plant material" refers broadly to a plant, a plant structure, a plant tissue, a plant seed or a plant cell that contains at least one heterologous gene in one or more of its cells.

The terms "transformants" or "transformed cells" include the primary transformed cell and cultures derived from that cell without regard to the number of transfers. All progeny may not be precisely identical in DNA content, due to deliberate or inadvertent mutations. Mutant progeny that have the same functionality as screened for in the originally transformed cell are included in the definition of transformants.

The term "wild-type" when made in reference to a gene refers to a gene that has the characteristics of a gene isolated from a naturally occurring source. The term "wild-type" when made in reference to a gene product refers to a gene product that has the characteristics of a gene product isolated from a naturally occurring source. A wild-type gene is that which is most frequently observed in a population and is thus arbitrarily designated the "normal" or "wild-type" form of the gene. In contrast, the term "modified" or "mutant" when made in reference to a gene or to a gene product refers, respectively, to a gene or to a gene product which displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "antisense" refers to a deoxyribonucleotide sequence whose sequence of deoxyribonucleotide residues is in reverse 5' to 3' orientation in relation to the sequence of deoxyribonucleotide residues in a sense strand of a DNA duplex. A "sense strand" of a DNA duplex refers to a strand in a DNA duplex that is transcribed by a cell in its natural state into a "sense mRNA." Thus an "antisense" sequence is a sequence having the same sequence as the non-coding strand in a DNA duplex. The term "antisense RNA" refers to a RNA transcript that is complementary to all or part of a target primary transcript or mRNA and that blocks the expression of a target gene by interfering with the processing, transport and/or translation of its primary transcript or mRNA. The complementarity of an antisense RNA may be with any part of the specific gene transcript, i.e., at the 5' non-coding sequence, 3' non-coding sequence, introns, or the coding sequence. In addition, as used herein, antisense RNA may contain regions of ribozyme sequences that increase the efficacy of antisense RNA to block gene expression. "Ribozyme" refers to a catalytic RNA and includes sequence-specific endoribonucleases. "Antisense inhibition" refers to the production of antisense RNA transcripts capable of preventing the expression of the target protein.

The term "posttranscriptional gene silencing" or "PTGS" refers to silencing of gene expression in plants after transcription, and appears to involve the specific degradation of mRNAs synthesized from gene repeats.

The term "overexpression" refers to the production of a gene product in transgenic organisms that exceeds levels of production in normal or non-transformed organisms. The term "cosuppression" refers to the expression of a foreign gene that has substantial homology to an endogenous gene resulting in the suppression of expression of both the foreign and the endogenous gene. The term "altered levels" refers to the production of gene product(s) in transgenic organisms in amounts or proportions that differ from that of normal or non-transformed organisms.

The term "recombinant" when made in reference to a nucleic acid molecule refers to a nucleic acid molecule that is comprised of segments of nucleic acid joined together by means of molecular biological techniques. The term "recombinant" when made in reference to a protein or a polypeptide refers to a protein molecule that is expressed using a recombinant nucleic acid molecule.

The term "isolated" when used in relation to a nucleic acid, as in "an isolated oligonucleotide" refers to a nucleic acid sequence that is identified and separated from at least one contaminant nucleic acid with which it is ordinarily associated in its natural source. Isolated nucleic acid is present in a form or setting that is different from that in which it is found in nature.

The term "purified" refers to molecules, either nucleic or amino acid sequences, that are removed from their natural environment, isolated or separated. An "isolated nucleic acid sequence" is therefore a purified nucleic acid sequence. "Substantially purified" molecules are at least 60% free, preferably at least 75% free, and more preferably at least 90% free from other components with which they are naturally associated. The term "purified" or "to purify" also refer to the removal of contaminants from a sample. The removal of contaminating proteins results in an increase in the percent of polypeptide of interest in the sample. In another example, recombinant polypeptides are expressed in plant, bacterial, yeast, or mammalian host cells and the polypeptides are purified by the removal of host cell proteins; the percent of recombinant polypeptides is thereby increased in the sample.

The term "sample" is used in its broadest sense. In one sense it can refer to a plant cell or tissue. In another sense, it is meant to include a specimen or culture obtained from any source, as well as biological and environmental samples. Biological samples may be obtained from plants or animals (including humans) and encompass fluids, solids, tissues, and gases. Environmental samples include environmental material such as surface matter, soil, water, and industrial samples. These examples are not to be construed as limiting the sample types applicable to the present invention.

DESCRIPTION OF THE INVENTION

The present invention relates to compositions and methods for controlling nematode infestation of plants or animals. In particular, the present invention provides vectors comprising sequences designed to control nematodes by RNA interference (RNAi) and transgenic plants transformed with such vectors. The compositions and methods of the present invention can be used to inhibit the growth and reproduction of a number of nematodes species, including, but not limited to plant parasitic nematodes and nematodes in the following genera: *Acontylus, Criconemella, Pseudhalenchus, Afenestrata, Cucullitylenchus, Lelenchus, Psilenchus, Aglenchus,*

*Cryphodera, Pterotylenchus, Allotylenchus, Cynipanguina, Macrotrophurus, Punctodera, Amplimerlinius, Malenchus, Anguina, Discocriconemella, Meloidodera, Radopholus, Antarctenchus, Ditylenchus, Meloidoderita, Rhizonema, Antarctylus, Dolichodera, Meloidogyne, Rotylenchulus, Aorolaimus, Dolichodorus, Meloinema, Rotylenchus, Aphasmatylenchus, Duotylenchus, Merlinius, Apratylenchoides, Miculenchus, Sarisodera, Atalodera, Ecphyadophora, Mitranema, Sauertylenchus, Atetylenchus, Ecphyadophoroides, Morulaimus, Scutellonema, Atylenchus, Epicharinema, Mukazia, Senegalonema, Eutylenchus, Sphaeronema, Bakemema, Nacobbodera, Subanguina, Basiria, Filenchus, Nacobbus, Sychnotylenchus, Basirienchus, Nagelus, Basiroides, Bellodera, Geocenamus, Neodolichodorus, Thada, Belonolaimus, Globodera, Neopsilenchus, Thecavermiculatus, Blandicephalanema, Gracilacus, Neothada, Trichotylenchus, Boleodorus, Gracilancea, Nothocriconemoides, Triversus, Brachydorus, Trophonema, Bursadera, Halenchus, Ogma, Trophotylenchulus, Helicotylenchus, Paraphelenchus, Trophurus, Cacopaurus, Hemicriconemoides, Pararotylenchus, Tylenchocriconema, Cactodera, Hemicycliophora, Paratrophurus, Tylenchorhynchus, Caloosia, Heterodera, Paratylenchus, Tylenchulus, Cambellenchus, Hirschmanniella, Pateracephalanema, Tylenchus, Carphodorus, Hoplolaimus, Pleurotylenchus, Tylodorus, Cephalenchus, Hoplotylus, Polenchus, Clavilenchus, Coslenchus, Hylonema, Pratylenchoides, Verutus, Criconema, Pratylenchus, Zygotylenchus*; and animal parasitic nematodes of the following genera: *Trichuris, Acylostoma, Necator, Strongyloides, Toxocara, Baylisacaris, Trichinella, Draccunculus, Filarioidea, Onchocerca, Loa, Dirofilaria*, and *Anisakis*.

I. RNAi

RNAi refers to the introduction of homologous double stranded RNA (dsRNA) to target a specific gene product, resulting in post transcriptional silencing of that gene. This phenomena was first reported in *Caenorhabditis elegans* by Guo and Kemphues (Par-1, A gene required for establishing polarity in *C. elegans* embryos, encodes a putative Ser/Thr kinase that is asymmetrically distributed, 1995, Cell, 81 (4) 611-620) and subsequently Fire et al. (Potent and specific genetic interference by double-stranded RNA in *Caenorhabditis elegans*, 1998, Nature 391: 806-811) discovered that it is the presence of dsRNA, formed from the annealing of sense and antisense strands present in the in vitro RNA preps, that is responsible for producing the interfering activity.

The present invention contemplates the use of RNA interference (RNAi) to downregulate the expression of genes needed for nematode viability and reproduction, thus reducing nematode infestation of plants. In both plants and animals, RNAi is mediated by RNA-induced silencing complex (RISC), a sequence-specific, multicomponent nuclease that destroys messenger RNAs homologous to the silencing trigger. RISC is known to contain short RNAs (approximately 22 nucleotides) derived from the double-stranded RNA trigger, although the protein components of this activity are unknown. However, the 22-nucleotide RNA sequences are homologous to the target gene that is being suppressed. Thus, the 22-nucleotide sequences appear to serve as guide sequences to instruct a multicomponent nuclease, RISC, to destroy the specific mRNAs.

Carthew has reported (Curr. Opin. Cell Biol. 13(2):244-248 (2001) that eukaryotes silence gene expression in the presence of dsRNA homologous to the silenced gene. Biochemical reactions that recapitulate this phenomenon generate RNA fragments of 21 to 23 nucleotides from the double-stranded RNA. These stably associate with an RNA endonuclease, and probably serve as a discriminator to select mRNAs. Once selected, mRNAs are cleaved at sites 21 to 23 nucleotides apart.

In preferred embodiments, the dsRNA used to initiate RNAi, may be isolated from native source or produced by known means, e.g., transcribed from DNA. The promoters and vectors described in more detail below are suitable for producing dsRNA. RNA is synthesized either in vivo or in vitro. In some embodiments, endogenous RNA polymerase of the cell may mediate transcription in vivo, or cloned RNA polymerase can be used for transcription in vivo or in vitro. In other embodiments, the RNA is provided transcription from a transgene in vivo or an expression construct. In some embodiments, the RNA strands are polyadenylated; in other embodiments, the RNA strands are capable of being translated into a polypeptide by a cell's translational apparatus. In still other embodiments, the RNA is chemically or enzymatically synthesized by manual or automated reactions. In further embodiments, the RNA is synthesized by a cellular RNA polymerase or a bacteriophage RNA polymerase (e.g., T3, T7, SP6). If synthesized chemically or by in vitro enzymatic synthesis, the RNA may be purified prior to introduction into the cell. For example, RNA can be purified from a mixture by extraction with a solvent or resin, precipitation, electrophoresis, chromatography, or a combination thereof. Alternatively, the RNA may be used with no or a minimum of purification to avoid losses due to sample processing. In some embodiments, the RNA is dried for storage or dissolved in an aqueous solution. In other embodiments, the solution contains buffers or salts to promote annealing, and/or stabilization of the duplex strands.

In some embodiments, the dsRNA is transcribed from the vectors as two separate stands. In other embodiments, the two strands of DNA used to form the dsRNA may belong to the same or two different duplexes in which they each form with a DNA strand of at least partially complementary sequence. When the dsRNA is thus-produced, the DNA sequence to be transcribed is flanked by two promoters, one controlling the transcription of one of the strands, and the other that of the complementary strand. These two promoters may be identical or different. In some embodiments, a DNA duplex provided at each end with a promoter sequence can directly generate RNAs of defined length, and which can join in pairs to form a dsRNA. See, e.g., U.S. Pat. No. 5,795,715, incorporated herein by reference. RNA duplex formation may be initiated either inside or outside the cell.

Inhibition is sequence-specific in that nucleotide sequences corresponding to the duplex region of the RNA are targeted for genetic inhibition. RNA molecules containing a nucleotide sequence identical to a portion of the target gene are preferred for inhibition. RNA sequences with insertions, deletions, and single point mutations relative to the target sequence have also been found to be effective for inhibition. Thus, sequence identity may optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the inhibitory RNA and the portion of the target gene is preferred. Alternatively, the duplex region of the RNA may be defined functionally as a nucleotide sequence that is capable of hybridizing with a portion of the target gene transcript. The length of the identical nucleotide sequences may be at least 25, 50, 100, 200, 300 or 400 bases.

There is no upper limit on the length of the dsRNA that can be used. For example, the dsRNA can range from about 21 base pairs (bp) of the gene to the full length of the gene or more. In one embodiment, the dsRNA used in the methods of the present invention is about 1000 bp in length. In another embodiment, the dsRNA is about 500 bp in length. In yet another embodiment, the dsRNA is about 22 bp in length. In some preferred embodiments, the sequences that mediate RNAi are from about 21 to about 23 nucleotides. That is, the isolated RNAs of the present invention mediate degradation of the target RNA (e.g., major sperm protein, chitin synthase, or RNA polymerase II).

The double stranded RNA of the present invention need only be sufficiently similar to natural RNA that it has the ability to mediate RNAi for the target RNA. In one embodiment, the present invention relates to RNA molecules of varying lengths that direct cleavage of specific mRNA to which their sequence corresponds. It is not necessary that there be perfect correspondence of the sequences, but the correspondence must be sufficient to enable the RNA to direct RNAi cleavage of the target mRNA. In a particular embodiment, the RNA molecules of the present invention comprise a 3' hydroxyl group. In some embodiments, the amount of target RNA (mRNA) is reduced in the cells of the target organism (e.g., *H. glycines*) exposed to target specific double stranded RNA as compared to target organisms that have not been exposed to target specific double stranded RNA.

Accordingly, in some embodiments, the present invention provides isolated RNA molecules (double-stranded or single-stranded) that are complementary to sequences required for nematode viability and/or reproduction. In some embodiments, the RNA molecules utilized mediate RNAi for embryonic lethal and sterile genes. Many genes with sterile or embryonic lethal RNAi phenotypes have been identified in high throughput screens (Fraser, A. G., Kamath, R. S., Zipperlen, P., Martinez-Campos, M., Sohrmann, M. and Ahringer, J. (2000). Functional genomic analysis of *C. elegans* chromosome I by systematic RNA interference. Nature 408, 325-330; Gonczy, P., Echeverri, G., Oegema, K., Coulson, A., Jones, S. J., Copley, R. R., Duperon, J., Oegema, J., Brehm, M., Cassin, E. et al. (2000). Functional genomic analysis of cell division in *C. elegans* using RNAi of genes on chromosome III. Nature 408, 331-336; Maeda, I., Kohara, Y., Yamamoto, M. and Sugimoto, A. (2001). Large-scale analysis of gene function in *Caenorhabditis elegans* by high-throughput RNAi. Curr Biol 11, 171-176). Much of this data and all of the sequences are available through WormBase (wormbase.org/). To date, over 2033 genes have been found to have an embryonic lethal RNAi phenotype and over 573 have a sterile RNAi phenotype. As described in more detail below and in the examples, these sequences may be screened for oral activity when expressed in plant tissue. In other embodiments, genes from this group that are specific to nematodes are utilized for RNAi so as to minimize interactions against endogenous proteins of plants, livestock and humans.

In some embodiments, probes that are specific for a nematode gene of interest are amplified from a DNA sample prepared from *C. elegans* by using primers designed from *C. elegans* genomic DNA or cDNA. Genes amplified from *C. elegans* DNA are then used as probes for homologous genes from a genomic or cDNA libraries prepared from the nematode of interest (e.g., *H. glycines*). In other embodiments, degenerate primers based on the *C. elegans* sequences are utilized to amplify the gene of interest from a library derived from the nematode of interest. These genes are then inserted into an expression vector so that a nematode double stranded RNA corresponding to the gene of interest is produced when the vector is used to transfect a plant.

Accordingly, in some embodiments, the present invention utilizes RNAi genes encoding dsRNA sequences that target nematode genes identified as having embryonic lethal or sterile RNAi phenotypes as identified by feeding nematodes dsRNA. The coding sequences for the target RNAs are available in public databases, including wormbase (wormbase.org). In still further embodiments, the genes utilized for RNAi are selected from the group consisting of major sperm protein, chitin synthase, and RNA polymerase II. The methods and compositions of the present invention have been exemplified for the control of *H. glycines*. However, it will be recognized that these materials and methods can be used the control of other nematodes. Accordingly the present invention provides the sequences for *H. glycines* major sperm protein (e.g., SEQ ID NO:1), chitin synthase (e.g., SEQ ID NO:18), and RNA polymerase II (e.g., SEQ ID NO:9). As described above, the entire coding sequence of the genes can be used to make dsRNA for RNAi, or, alternatively, subsequences can be utilized. The following table presents other suitable subsequences for use in RNAi. Both these sequences and their complements are expressed from vectors as described herein to form double stranded RNA molecules.

TABLE 1

Sequences for RNAi

Major sperm protein subsequences

| | |
|---|---|
| SEQ ID NO:25 | CGGGGTCGAAGGCGTCNCAGAANACGGCCAC GTTGACAGATTCCTTTGGGCCGANCACTCCG |
| SEQ ID NO:26 | TCCGGCGGGTTCATGTTGATNCGCTTCGGTTTG |
| SEQ ID NO:27 | CGTGGTGTCGGCTGGGTCCGGTGT GTTGGTCCACTCCGC |
| SEQ ID NO:28 | GGCACGTTGGTCCACGCCACG GTCACACGGTCGTCCTTGGTGTCCTCGCTGC |
| SEQ ID NO:29 | GGCGTCNCAGAANACGGCCAC GTTGACAGATTCCTTTGGGCCGANCACTCCG |
| SEQ ID NO:30 | GGGCGGTTCCGGCACGTTGGTCCACGCCACG GTCACACGGTCGTCCTTGGTGTCCTCGCTGC |

RNA polymerase II subsequences

| | |
|---|---|
| SEQ ID NO:31 | AATCTGTCAACGTGGCCGTNTTCTGNGACGCC TTCGACCCCGGCAGCGAGGACACCAAGGACGA CCGTGTGACCGTGGCGTGGACCAACGTGCCGG AACCGCCCGGCGCCGCCGCCGCCGCGGAGTGG ACCAACACACCGGACCCAGCCGACACCACGTT CAAG |
| SEQ ID NO:32 | GGTCGTCCTTGGTGTCCTCGCTGCCGGGGTCGA AGGCGTCNCAGAANACGGCCACGTTGACAGATT CCTTTGGGCCGANCACTCCGTCCGGCGGGTTCA TGTTGATNCGCTTCGGTTTG |
| SEQ ID NO:33 | TTGAACGTGGTGTCGGCTGGGTCCGGTGTGTT GGTCCACTCCGCGGCGGCGGCGGCGCCGGGCG GTTCCGGCACGTTGGTCCACGCCACGGTCACAC GGTCGTCCTTGGTGTCCTCGCTGCCGGGGTCGA |
| SEQ ID NO:34 | GGTCGTCCTTGGTGTCCTCGCTGCCGGGGTCGA AGGCGTCNCAGAANACGGCCACGTTGACAGATT |
| SEQ ID NO:35 | TTCAAGACCACCAAACCGAAGCGNATCAACAT GAACCCGCCGGACGGAGTGNTCGGCCCAAAGG AATCTGTCAACGTGGCCGTNTTCTGNGACGCC TTCGACCCCGGCAGCGAGGACACCAAGGACGA |
| SEQ ID NO:36 | CCGTGTGACCGTGGCGTGGACCAACGTGCCGG AACCGCCCGGCGCCGCCGCCGCCGCGGAGTGG ACCAACACACCGGACCCAGCCGACACCACGTT |
| SEQ ID NO:37 | ATCATGTCCATGTTGAGGTGACGAAGCATCCTTCCAT CAGACGTTGTACTCGATCGGCAAGTTCTTGCGGC GCACCATCCCGTCTCCCTGGAACCA |

TABLE 1-continued

Sequences for RNAi

Chitin synthase sequences

SEQ ID NO:38  TGGTTTGGTACCAAAAGTTCGAGTACGCAATCGC
              CCATTGGTTCCAAAAG
SEQ ID NO:39  GCTGCTGAGCATGTGTTCGGCTGTGTTTTGTGTGC
              CCCCGGTAGCTTCTC
SEQ ID NO:40  TCTGTTTCGTGCTTCTGCTCTCATGGATGACAATGT
              GATGCACAAATACA
SEQ ID NO:41  CCAAAANTGCCTCCGAACCNACGACNATTTTGTTC
              AGTATGATCAAGGCGAAGACCCGATGGA
SEQ ID NO:42  TCTGTTTCGTGCTTCTGCTCTCATGGATGACAATGT
              GATGCACAAATACACCAAAANTGCCTCCGAACCN
              ACGACNATTTTGTTCAGTATGATCAAGGCG
SEQ ID NO:43  TCTGTTTCGTGCTTCTGCTCTCATGGATGACAATGT
              GATGCACAAATACACCAAAANTGCCTCCGAACCNA
              CGACNATTTTGTTCAGTATGATCAAGGCG
SEQ ID NO:44  TCTGTTTCGTGCTTCTGCTCTCATGGATGACAATGTG
              ATGCACAAATACACCAAA

Additionally, homologous sequences from other nematodes may be utilized for targeting the corresponding species of nematode. For example, a number of homologous Major sperm protein genes are known, including those identified by the following GenBank Accession numbers: GI403083, GI403087, GI17535306, GI159665, GI1373354, GI1373307, GI159897, GI12055908, and GI12055882 among others. Such sequences can be conveniently identified by conducting BLASTN of BLASTP searches of GenBank as appropriate.

Other genes that are useful for targeting include those described in Kamath et al., Effectiveness of specific RNA-mediated interference through ingested double-stranded RNA in *Caenorhabditis elegans*. *Genome Biology*, 2(1):research0002.1-0002.10 (2000). These genes are identified in the following Table:

TABLE 2

| Gene(s) | Feeding phenotype | Gene information |
|---|---|---|
| K04G2.8a | Unc, Bmd, Lvl | apr-1 (APC-related) |
| F18C12.2a | Emb, Unc, Mlt, Bmd | DNA-J domain |
| ZK265.5, 6* | Gro | G-protein-coupled receptor/unknown function |
| T01G9.4 | Emb, Gro, Clr | kup-2 (unknown function) |
| T01G9.5 | Emb | mei-1 (meiotic spindle formation) |
| T01G9.6a | Emb, Gro, Pvl | kin-10 (CKII-beta subunit) |
| F52B5.6 | Emb, Ste | Ribosomal protein L25 |
| T19A6.2a | Gro | Ynr053p-like protein |
| D1081.2 | Unc, Prz | MADS domain |
| D1081.8 | Emb | Myb-like DNA-binding domain |
| K02B12.1 | Unc, Mlt | ceh-6 (POU homeodomain protein) |
| K02B12.3 | Ste, Gro | WD domains |
| K02B12.8 | Him | Unknown function |
| Gpb-1 | | |
| gpb-1 | Mtl | Identity of corresponding gene under review |
| par-1 | Mtl | required for establishing polarity |
| par-2 | Mtl | required for blastomere asymmetry |
| par-3 | Mtl | control of cleavage spindle orientation |
| par-6 | Mtl | involved in the establishment of asymmetry |
| cyk-1 | Mtl | required for cytokinesis |
| skn-1 | Mtl | required for mitotic spindle orientation |

TABLE 2-continued

| Gene(s) | Feeding phenotype | Gene information |
|---|---|---|
| dnc-1 | Mtl | required for mitotic spindle orientation |
| bir-1 | Mtl | inhibitor of apoptosis protein (IAP) homologue |
| pal-1 | Mtl | required to specify the somatic identity of one posterior blastomere in the 4 cell embryo |
| dif-1 | Mtl | Mitochondrial Transporters |
| plk-1 | Mtl | Polo-like kinase PLK-1 is required for nuclear envelope breakdown and the completion of meiosis |
| dhc-1 | Mtl, Emb | Dynein Heavy Chain |
| mex-3 | Mtl | regulates blastomere identity |

Bmd, body morphology defect; Clr, clear; Emb, embryonic lethal; Gro, slow growth; Him, high incidence of males; Lvl, larval lethal (death at any larval stage); Mlt, molting defect (old cuticle remains attached); Prz, paralyzed; Pvl, protruding vulva; Ste, sterile; Unc, uncoordinated; Mtl, maternal lethal.

II. Transgenic Plants

In some embodiments, the present invention provides transgenic plants that express dsRNA molecules that correspond to target molecules in desired nematode species. It is contemplated that nematodes feeding on the transgenic plants ingest the dsRNA molecules, which in turn decrease the abundance of target RNA within the nematode species. By targeting genes that are required for fertility or fitness of the nematode, nematode growth and reproduction is reduced thus reducing nematode induced plant damage (e.g., root cysts).

A heterologous gene encoding a RNAi gene of the present invention, which includes variants of the RNAi gene, includes any suitable sequence that encodes an double stranded molecule specific for a nematode target RNA. Preferably, the heterologous gene is provided within an expression vector such that transformation with the vector results in expression of the double stranded RNA molecule; suitable vectors are described below.

In yet other embodiments of the present invention, a transgenic plant comprises a heterologous gene encoding a RNAi gene of the present invention operably linked to an inducible promoter, and is grown either in the presence of the an inducing agent, or is grown and then exposed to an inducing agent. In still other embodiments of the present invention, a transgenic plant comprises a heterologous gene encoding a RNAi gene of the present invention operably linked to a promoter which is either tissue specific or developmentally specific, and is grown to the point at which the tissue is developed or the developmental stage at which the developmentally-specific promoter is activated. Such promoters include seed and root specific promoters. In still other embodiments of the present invention, the transgenic plant comprises a RNAi gene of the present invention operably linked to constitutive promoter. In further embodiments, the transgenic plants of the present invention express at least one double stranded RNA molecule at a level sufficient to reduce the proliferation of nematodes as compared to the proliferation of nematodes observed in a nontransgenic plant.

1. Plants

The methods of the present invention are not limited to any particular plant. Indeed, a variety of plants are contemplated, including but not limited to soybean, wheat, oats, milo, sorghum, cotton, tomato, potato, tobacco, pepper, rice, corn, barley, Brassica, Arabidopsis, sunflower, poplar, pineapple, banana, turf grass, and pine. Many commercial cultivars can be transformed with heterologous genes. In cases where that is not possible, non-commercial cultivars of plants can be transformed, and the trait for expression of the RNAi gene of the present invention moved to commercial cultivars by breeding techniques well-known in the art.

2. Vectors

The methods of the present invention contemplate the use of at least one heterologous gene encoding a RNAi gene of the present invention. Heterologous genes intended for expression in plants are first assembled in expression cassettes comprising a promoter. Methods which are well known to those skilled in the art may be used to construct expression vectors containing a heterologous gene and appropriate transcriptional and translational control elements. These methods include in vitro recombinant DNA techniques, synthetic techniques, and in vivo genetic recombination. Such techniques are widely described in the art (See e.g., Sambrook. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York, N.Y).

In general, these vectors comprise a nucleic acid sequence of the invention encoding a RNAi gene of the present invention (as described above) operably linked to a promoter and other regulatory sequences (e.g., enhancers, polyadenylation signals, etc.) required for expression in a plant.

Promoters include but are not limited to constitutive promoters, tissue-, organ-, and developmentally-specific promoters, and inducible promoters. Examples of promoters include but are not limited to: constitutive promoter 35S of cauliflower mosaic virus; a wound-inducible promoter from tomato, leucine amino peptidase ("LAP," Chao et al. (1999) Plant Physiol 120: 979-992); a chemically-inducible promoter from tobacco, Pathogenesis-Related 1 (PR1) (induced by salicylic acid and BTH (benzothiadiazole-7-carbothioic acid S-methyl ester)); a tomato proteinase inhibitor II promoter (PIN2) or LAP promoter (both inducible with methyl jasmonate); a heat shock promoter (U.S. Pat. No. 5,187,267); a tetracycline-inducible promoter (U.S. Pat. No. 5,057,422); and seed-specific promoters, such as those for seed storage proteins (e.g., phaseolin, napin, oleosin, and a promoter for soybean beta conglycin (Beachy et al. (1985) EMBO J. 4: 3047-3053)). In some preferred embodiments, the promoter is a phaseolin promoter. All references cited herein are incorporated in their entirety.

The expression cassettes may further comprise any sequences required for expression of mRNA. Such sequences include, but are not limited to transcription terminators, enhancers such as introns, viral sequences, and sequences intended for the targeting of the gene product to specific organelles and cell compartments.

A variety of transcriptional terminators are available for use in expression of sequences using the promoters of the present invention. Transcriptional terminators are responsible for the termination of transcription beyond the transcript and its correct polyadenylation. Appropriate transcriptional terminators and those which are known to function in plants include, but are not limited to, the CaMV 35S terminator, the tml terminator, the pea rbcS E9 terminator, and the nopaline and octopine synthase terminator (See e.g., Odell et al. (1985) Nature 313:810; Rosenberg et al. (1987) Gene, 56:125; Guerineau et al. (1991) Mol. Gen. Genet., 262:141; Proudfoot (1991) Cell, 64:671; Sanfacon et al. Genes Dev., 5:141; Mogen et al. (1990) Plant Cell, 2:1261; Munroe et al. (1990) Gene, 91:151; Ballad et al. (1989) Nucleic Acids Res. 17:7891; Joshi et al. (1987) Nucleic Acid Res., 15:9627).

In addition, in some embodiments, constructs for expression of the gene of interest include one or more of sequences found to enhance gene expression from within the transcriptional unit. These sequences can be used in conjunction with the nucleic acid sequence of interest to increase expression in plants. Various intron sequences have been shown to enhance expression, particularly in monocotyledonous cells. For example, the introns of the maize Adh1 gene have been found to significantly enhance the expression of the wild-type gene under its cognate promoter when introduced into maize cells (Calais et al. (1987) Genes Develop. 1: 1183). Intron sequences have been routinely incorporated into plant transformation vectors, typically within the non-translated leader.

In some embodiments of the present invention, the construct for expression of the nucleic acid sequence of interest also includes a regulator such as a nuclear localization signal (Calderone et al. (1984) Cell 39:499; Lassoer et al. (1991) Plant Molecular Biology 17:229), a plant translational consensus sequence (Joshi (1987) Nucleic Acids Research 15:6643), an intron (Luehrsen and Walbot (1991) Mol. Gen. Genet. 225:81), and the like, operably linked to the nucleic acid sequence encoding ADS.

In preparing a construct comprising a nucleic acid sequence encoding a RNAi gene of the present invention, various DNA fragments can be manipulated, so as to provide for the DNA sequences in the desired orientation (e.g., sense or antisense) orientation. For example, adapters or linkers can be employed to join the DNA fragments or other manipulations can be used to provide for convenient restriction sites, removal of superfluous DNA, removal of restriction sites, or the like. For this purpose, in vitro mutagenesis, primer repair, restriction, annealing, resection, ligation, or the like is preferably employed, where insertions, deletions or substitutions (e.g., transitions and transversions) are involved.

Numerous transformation vectors are available for plant transformation. The selection of a vector for use will depend upon the preferred transformation technique and the target species for transformation. For certain target species, different antibiotic or herbicide selection markers are preferred. Selection markers used routinely in transformation include the nptII gene which confers resistance to kanamycin and related antibiotics (Messing and Vierra (1982) Gene 19: 259; Bevan et al. (1983) Nature 304:184), the bar gene which confers resistance to the herbicide phosphinothricin (White et al. (1990) Nucl Acids Res. 18:1062; Spencer et al. (1990) Theor. Appl. Genet. 79:625), the hph gene which confers resistance to the antibiotic hygromycin (Blochlinger and Diggelmann (1984) Mol. Cell. Biol. 4:2929), and the dhfr gene, which confers resistance to methotrexate (Bourouis et al. (1983) EMBO J., 2:1099).

In some preferred embodiments, the vector is adapted for use in an Agrobacterium mediated transfection process (See e.g., U.S. Pat. Nos. 5,981,839; 6,051,757; 5,981,840; 5,824,877; and 4,940,838; all of which are incorporated herein by reference). Construction of recombinant Ti and Ri plasmids in general follows methods typically used with the more common bacterial vectors, such as pBR322. Additional use can be made of accessory genetic elements sometimes found with the native plasmids and sometimes constructed from foreign sequences. These may include but are not limited to structural genes for antibiotic resistance as selection genes.

There are two systems of recombinant Ti and Ri plasmid vector systems now in use. The first system is called the "cointegrate" system. In this system, the shuttle vector containing the gene of interest is inserted by genetic recombination into a non-oncogenic Ti plasmid that contains both the cis-acting and trans-acting elements required for plant transformation as, for example, in the pMLJ1 shuttle vector and the non-oncogenic Ti plasmid pGV3850. The second system is called the "binary" system in which two plasmids are used; the gene of interest is inserted into a shuttle vector containing the cisacting elements required for plant transformation. The other necessary functions are provided in trans by the non-oncogenic Ti plasmid as exemplified by the pBIN19 shuttle vector and the non-oncogenic Ti plasmid PAL4404. Some of these vectors are commercially available.

In other embodiments of the invention, the nucleic acid sequence of interest is targeted to a particular locus on the plant genome. Site-directed integration of the nucleic acid sequence of interest into the plant cell genome may be achieved by, for example, homologous recombination using Agrobacterium-derived sequences. Generally, plant cells are incubated with a strain of Agrobacterium which contains a targeting vector in which sequences that are homologous to a DNA sequence inside the target locus are flanked by Agrobacterium transfer-DNA (T-DNA) sequences, as previously described (U.S. Pat. No. 5,501,967). One of skill in the art knows that homologous recombination may be achieved using targeting vectors which contain sequences that are homologous to any part of the targeted plant gene, whether belonging to the regulatory elements of the gene, or the coding regions of the gene. Homologous recombination may be achieved at any region of a plant gene so long as the nucleic acid sequence of regions flanking the site to be targeted is known.

In yet other embodiments, the nucleic acids of the present invention are utilized to construct vectors derived from plant (+) RNA viruses (e.g., brome mosaic virus, tobacco mosaic virus, alfalfa mosaic virus, cucumber mosaic virus, tomato mosaic virus, and combinations and hybrids thereof). Generally, the inserted ADS polynucleotide of the present invention can be expressed from these vectors as a fusion protein (e.g., coat protein fusion protein) or from its own subgenomic promoter or other promoter. Methods for the construction and use of such viruses are described in U.S. Pat. Nos. 5,846,795; 5,500,360; 5,173,410; 5,965,794; 5,977,438; and 5,866,785, all of which are incorporated herein by reference.

In some embodiments of the present invention the nucleic acid sequence of interest is introduced directly into a plant. One vector useful for direct gene transfer techniques in combination with selection by the herbicide Basta (or phosphinothricin) is a modified version of the plasmid pCIB246, with a CaMV 35S promoter in operational fusion to the E. coli GUS gene and the CaMV 35S transcriptional terminator (WO 93/07278).

3. Transformation Techniques

Once a nucleic acid sequence encoding an ADS of the present invention is operatively linked to an appropriate promoter and inserted into a suitable vector for the particular transformation technique utilized (e.g., one of the vectors described above), the recombinant DNA described above can be introduced into the plant cell in a number of art-recognized ways. Those skilled in the art will appreciate that the choice of method might depend on the type of plant targeted for transformation. In some embodiments, the vector is maintained episomally. In other embodiments, the vector is integrated into the genome.

In some embodiments, the vector is introduced through ballistic particle acceleration using devices (e.g., available from Agracetus, Inc., Madison, Wis. and Dupont, Inc., Wilmington, Del.). (See e.g., U.S. Pat. No. 4,945,050; and McCabe et al. (1988) Biotechnology 6:923). See also, Weissinger et al. (1988) Annual Rev. Genet. 22:421; Sanford et al. (1987) Particulate Science and Technology, 5:27 (onion); Svab et al. (1990) Proc. Natl. Acad. Sci. USA, 87:8526 (tobacco chloroplast); Christou et al. (1988) Plant Physiol., 87:671 (soybean); McCabe et al. (1988) Bio/Technology 6:923 (soybean); Klein et al. (1988) Proc. Natl. Acad. Sci. USA, 85:4305 (maize); Klein et al. (1988) Bio/Technology, 6:559 (maize); Klein et al. (1988) Plant Physiol., 91:4404 (maize); Fromm et al. (1990) Bio/Technology, 8:833; and Gordon-Kamm et al. (1990) Plant Cell, 2:603 (maize); Koziel et al. (1993) Biotechnology, 11:194 (maize); Hill et al. (1995) Euphytica, 85:119 and Koziel et al. (1996) Annals of the New York Academy of Sciences 792:164; Shimamoto et al. (1989) Nature 338: 274 (rice); Christou et al. (1991) Biotechnology, 9:957 (rice); Datta et al. (1990) Bio/Technology 8:736 (rice); European Patent Application EP 0 332 581 (orchardgrass and other Pooideae); Vasil et al. (1993) Biotechnology, 11: 1553 (wheat); Weeks et al. (1993) Plant Physiol., 102: 1077 (wheat); Wan et al. (1994) Plant Physiol. 104: 37 (barley); Jahne et al. (1994) Theor. Appl. Genet. 89:525 (barley); Knudsen and Muller (1991) Planta, 185:330 (barley); Umbeck et al. (1987) Bio/Technology 5: 263 (cotton); Casas et al. (1993) Proc. Natl. Acad. Sci. USA 90:11212 (sorghum); Somers et al. (1992) Bio/Technology 10:1589 (oat); Torbert et al. (1995) Plant Cell Reports, 14:635 (oat); Weeks et al. (1993) Plant Physiol., 102:1077 (wheat); Chang et al., WO 94/13822 (wheat) and Nehra et al. (1994) The Plant Journal, 5:285 (wheat).

In other embodiments, direct transformation in the plastid genome is used to introduce the vector into the plant cell (See e.g., U.S. Pat. Nos. 5,451,513; 5,545,817; 5,545,818; PCT application WO 95/16783). The basic technique for chloroplast transformation involves introducing regions of cloned plastid DNA flanking a selectable marker together with the nucleic acid encoding the RNA sequences of interest into a suitable target tissue (e.g., using biolistics or protoplast transformation with calcium chloride or PEG). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin and/or streptomycin are utilized as selectable markers for transformation (Svab et al. (1990) PNAS, 87:8526; Staub and Maliga, (1992) Plant Cell, 4:39). The presence of cloning sites between these markers allowed creation of a plastid targeting vector introduction of foreign DNA molecules (Staub and Maliga (1993) EMBO J., 12:601). Substantial increases in transformation frequency are obtained by replacement of the recessive rRNA or r-protein antibiotic resistance genes with a dominant selectable marker, the bacterial aadA gene encoding the spectinomycin-detoxifying enzyme aminoglycoside-3'-adenyltransferase (Svab and Maliga (1993) PNAS, 90:913). Other selectable markers useful for plastid transformation are known in the art and encompassed within the scope of the present invention. Plants homoplasmic for plastid genomes containing the two nucleic acid sequences separated by a promoter of the present invention are obtained, and are preferentially capable of high expression of the RNAs encoded by the DNA molecule.

In other embodiments, vectors useful in the practice of the present invention are microinjected directly into plant cells by use of micropipettes to mechanically transfer the recombinant DNA (Crossway (1985) Mol. Gen. Genet, 202:179). In still other embodiments, the vector is transferred into the plant cell by using polyethylene glycol (Krens et al. (1982) Nature, 296:72; Crossway et al. (1986) BioTechniques, 4:320); fusion of protoplasts with other entities, either minicells, cells, lysosomes or other fusible lipid-surfaced bodies (Fraley et al. (1982) Proc. Natl. Acad. Sci., USA, 79:1859); protoplast transformation (EP 0 292 435); direct gene transfer (Paszkowski et al. (1984) EMBO J., 3:2717; Hayashimoto et al. (1990) Plant Physiol. 93:857).

In still further embodiments, the vector may also be introduced into the plant cells by electroporation (Fromm, et al. (1985) Proc. Natl Acad. Sci. USA 82:5824; Riggs et al. (1986) Proc. Natl. Acad. Sci. USA 83:5602). In this technique, plant protoplasts are electroporated in the presence of plasmids containing the gene construct. Electrical impulses of high field strength reversibly permeabilize biomembranes allowing the introduction of the plasmids. Electroporated plant protoplasts reform the cell wall, divide, and form plant callus.

In addition to direct transformation, in some embodiments, the vectors comprising a nucleic acid sequence encoding a RNAi gene of the present invention are transferred using Agrobacterium-mediated transformation (Hinchee et al. (1988) Biotechnology, 6:915; Ishida et al. (1996) Nature Biotechnology 14:745). Agrobacterium is a representative genus of the gram-negative family Rhizobiaceae. Its species are responsible for plant tumors such as crown gall and hairy root disease. In the dedifferentiated tissue characteristic of the tumors, amino acid derivatives known as opines are produced and catabolized. The bacterial genes responsible for expression of opines are a convenient source of control elements for chimeric expression cassettes. Heterologous genetic sequences (e.g., nucleic acid sequences operatively linked to a promoter of the present invention), can be introduced into appropriate plant cells, by means of the Ti plasmid of *Agrobacterium tumefaciens*. The Ti plasmid is transmitted to plant cells on infection by *Agrobacterium tumefaciens*, and is stably integrated into the plant genome (Schell (1987) Science, 237: 1176). Species which are susceptible infection by Agrobacterium may be transformed in vitro. Alternatively, plants may be transformed in vivo, such as by transformation of a whole plant by Agrobacteria infiltration of adult plants, as in a "floral dip" method (Bechtold N, Ellis J, Pelletier G (1993) Cr. Acad. Sci. III-Vie 316: 1194-1199).

4. Regeneration

After selecting for transformed plant material that can express the heterologous gene encoding a RNAi gene of the present invention, whole plants are regenerated. Plant regeneration from cultured protoplasts is described in Evans et al. (1983) Handbook of Plant Cell Cultures, Vol. 1: (MacMillan Publishing Co. New York); and Vasil I. R. (ed.), Cell Culture and Somatic Cell Genetics of Plants, Acad. Press, Orlando, Vol. I (1984), and Vol. III (1986). It is known that many plants can be regenerated from cultured cells or tissues, including but not limited to all major species of sugarcane, sugar beet, cotton, fruit and other trees, legumes and vegetables, and monocots (e.g., the plants described above). Means for regeneration vary from species to species of plants, but generally a suspension of transformed protoplasts containing copies of the heterologous gene is first provided. Callus tissue is formed and shoots may be induced from callus and subsequently rooted.

Alternatively, embryo formation can be induced from the protoplast suspension. These embryos germinate and form mature plants. The culture media will generally contain various amino acids and hormones, such as auxin and cytokinins. Shoots and roots normally develop simultaneously. Efficient regeneration will depend on the medium, on the genotype, and on the history of the culture. The reproducibility of regeneration depends on the control of these variables.

5. Generation of Transgenic Lines

Transgenic lines are established from transgenic plants by tissue culture propagation. The presence of nucleic acid sequences encoding a RNAi gene of the present invention (including mutants or variants thereof) may be transferred to related varieties by traditional plant breeding techniques.

These transgenic lines are then utilized for evaluation of oil production and other agronomic traits.

III. Animal Feeds Containing dsRNA Molecules

The present invention provides animals feeds comprising dsRNA molecules derived from plants. In some embodiments, the dsRNA molecules are present in seeds and seed products derived from the transgenic plants described above. It is contemplated that providing feed containing dsRNA to animals results in a decrease in nematode infestation of the animals. Suitable methods for formulating feed are well known in the art. Feeds for a variety of animals may be formulated, including but not limited to, pigs, cattle, sheep, chickens, turkeys and other poultry, fish, horses, dogs, cats, and rabbits.

In other embodiments, the transgenic plant material is encapsulated. For example, in some embodiments, tablets or capsules of the present invention are coated with an enteric coating which dissolves at a pH of about 6.0 to 7.0. A suitable enteric coating which dissolves in the small intestine but not in the stomach is cellulose acetate phthalate. Further details on techniques for formulation for and administration and administration may be found in the latest edition of *Remington's Pharmaceutical Sciences* (Maack Publishing Co., Easton, Pa.).

In further embodiments, the present invention provides pharmaceutical compositions comprising transgenic plant material derived from transgenic plants expressing a nematode double stranded RNA. In some embodiments, the pharmaceutical compositions of the present invention can be formulated using pharmaceutically acceptable carriers well known in the art in dosages suitable for oral administration. Such carriers enable the pharmaceutical compositions to be formulated as tablets, pills, capsules, liquids, gels, syrups, slurries, suspensions and the like, for oral or nasal ingestion by a subject to be treated.

Pharmaceutical compositions suitable for use in the present invention include compositions wherein the active ingredients are contained in an effective amount to achieve the intended purpose. Determination of effective amounts is well within the capability of those skilled in the art, especially in light of the disclosure provided herein. In some embodiments, a therapeutically effective dose refers to that amount of plant material that ameliorates symptoms of the disease state (i.e., nematode infestation). Toxicity and therapeutic efficacy of such compounds can be determined by standard pharmaceutical procedures in in vitro models or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds that exhibit large therapeutic indices are preferred. The data obtained from these cell culture assays and additional animal studies can be used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

In addition to the active ingredients these pharmaceutical compositions may contain suitable pharmaceutically acceptable carriers comprising excipients and auxiliaries that facilitate processing of the active compounds into preparations that can be used pharmaceutically. The preparations formulated for oral administration may be in the form of tablets, dragees, capsules, or solutions.

The pharmaceutical compositions of the present invention may be manufactured in a manner that is itself known (e.g., by means of conventional mixing, dissolving, granulating, dragee-making, levigating, emulsifying, encapsulating, entrapping or lyophilizing processes).

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, etc; cellulose such as methyl cellulose, hydroxypropylmethyl-cellulose, or sodium carboxymethyl-cellulose; and gums including arabic and tragacanth; and proteins such as gelatin and collagen. If desired, disintegrating or solubilizing agents may be added, such as the cross-linked polyvinyl pyrrolidone, agar, alginic acid or a salt thereof such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, (i.e., dosage).

Pharmaceutical preparations that can be used orally include push-fit capsules made of gelatin, as well as soft, sealed capsules made of gelatin and a coating such as glycerol or sorbitol. The push-fit capsules can contain the active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

EXPERIMENTAL

The following examples are provided in order to demonstrate and further illustrate certain preferred embodiments and aspects of the present invention and are not to be construed as limiting the scope thereof.

In the experimental disclosures which follow, the following abbreviations apply: N (normal); M (molar); mM (millimolar); μM (micromolar); mol (moles); mmol (millimoles); μmol (micromoles); nmol (nanomoles); pmol (picomoles); g (grams); mg (milligrams); μg (micrograms); ng (nanograms); l or L (liters); ml (milliliters); μl (microliters); cm (centimeters); mm (millimeters); μm (micrometers); nm (nanometers); ° C. (degrees Centigrade).

Example 1

Construction of Major Sperm Protein RNAi Gene

This Example describes the construction of the expression construct for MSP dsRNA for use in RNAi. Conserved regions of the MSP gene for various nematodes were found using "Block Maker". Degenerate primers were synthesized and a partial gene fragment was amplified from SCN genomic DNA. The fragment was cloned into pGEM-T Easy vector, sequenced, and used for a BLAST search in GenBank. The cloned sequence showed homology with MSP genes from other nematodes. The fragment was used to probe a cDNA library made from J2 juveniles.

A subclone was identified in a SCNJ2 cDNA lambda library and sequenced. This sequence is presented in FIG. 1 as SEQ ID NO:1. A T7 primer (5' gta ata cga ctc act ata ggg c 3'; SEQ ID NO:2) and MSP specific primer (5' cca tgg ctg cag gcc ttc aag acc ac 3'; SEQ ID NO:3; reverse compliment identified by double underline in FIG. 1) were used to amplify an approximately 600 base pair fragment of MSP. The MSP specific primer (SEQ ID NO:3) was designed to introduce NcoI (C'CATGG) and PstI (CTGCA'G) sites at the 5' end of the amplified product. The resulting amplified fragment was then subcloned into pGEM-T. The subcloned sequence was then excised from the vector by digestion with BamHI and EcoRI to provide SEQ ID NO: 45 (FIG. 2B). The EcoRI site is located in the pGEM-T vector, while the BamHI site is located in the MSP coding region. The resulting fragment was then digested with XhoI and PstI to provide SEQ ID NO:4 (FIG. 2A). The reverse complement of SEQ ID NO:4 is provided in FIG. 3 as SEQ ID NO:5. SEQ ID NOS: 45 and 5 were then sequentially cloned into pGEM3zf(+) into EcoRI/BamHI and SalI/PstI sites to provide the assembled MSPi sequence (SEQ ID NO:6; FIG. 4; the loop sequence separating the sense and antisense sequences is underlined).

The MSPi sequence was removed excised from the plasmid by a NcoI/HindIII digest and cloned into pATACTCV (Arabidopsis actin-2 promoter (An et al., Strong, constitutive expression of the Arabidopsis ACT2/ACT8 actin subclass in vegetative tissues. Plant Journal, 10 (1): 107-121 (1996)) to provide plasmid (pATMSPi). The NcoI site is at the 5' end of pATMSPi, while the HindIII site is at the 3' end of the plasmid.

Example 2

RNA Polymerase II Construct Design

This Example describes the construction of an RNA polymerase II RNAi gene. Degenerate primers were used to retrieve RNA polymerase II sequence from *H. glycines*. Since *H. glycines* RNA polymerase II sequence was unknown, the primers had to be designed using sequence from *C. elegans* and three other related organisms-Artemia salina (brine shrimp), Helobdella stagnalis (leech), and Ilyanassa obsoleta (eastern mud snail). The RNA polymerase II sequences of these four organisms were copied into Blockmaker (blocks-.fhcrc.org). The blocks formed from Blockmaker were then copied into Codehop to make degenerate primers. The sequences were also copied into Clustalw, which, like Blockmaker, is a multiple sequence alignment tool. The advantage of using Clustalw is that it provides a view of the entire alignment of the sequences rather than just blocks of alignments. Clustalw also points out regions of the alignment that have very tight homology throughout the different organisms. Codehop constructs degenerate primers from the blocks assembled in Blockmaker. Degenerate primers were chosen that had tight homology in the sequence alignments in Clustalw, a GC content greater than 45%, degeneracy no greater than 16, and amino acids in the 3' end of the primer that are coded for by only 1 or 2 codons.

The degenerate primer pair dRP2L_F/dRP2T_R1 was chosen from the degenerate primers made in Codehop.

```
                                                         (SEQ ID NO:11)
RP2_KpnF1B primer: GACGGTACCGGCAGTGTCAATGTTATCCGAAC
32mer—This primer adds a Kpn I site to the anti-
sense
fragment (underlined)

(SEQ ID NO:12)
RP2_BamRB primer: ATCGGATCCTCCAATGGTGTGTCCCTCGG
29mer—This primer adds a Bam HI site to the anti-
sense
fragment (underlined)
```

```
dRP2L_F primer:  5'-CCA ACC CTG CAC AAA ATG WSN ATG ATG-3' 27mer.(SEQ ID NO:7)

dRP2T_R1 primer: 5'-CAG AAT TCG GTT CAC TTG RTT YTC RAA-3' 27mer.(SEQ ID NO:8)
```

The dRP2L_F/dRP2T_R1 primer pair successfully amplified an ~1.0 kilobase fragment from genomic *H. glycines* DNA. The fragment was cloned into a PGEM-T-easy vector and five clones were found to have the ~1.0 kb fragment. Each of the clones were sequenced using SP6 and T7. The sequence of the clones was identical. One of the clones was randomly chosen for further sequence analysis. The sequence of this clone is provided FIG. 5 as SEQ ID NO:9.

SEQ ID NO:9 was used in a blastx search which compared it to a protein database (ncbi.nlm.nih.gov/BLAST/). The blastx search confirmed that the sequence of clone 6 was RNA polymerase II. Tblastx was also used which blasted the degenerate nucleotide sequence against a translated database. Tblastx aided in the location of exons and introns in the degenerate sequence. It was necessary to locate the exon regions of the sequence because the construct must be designed from regions that are transcribed (i.e. exons). From tblastx, it was estimated that an exon occurred between base pair 555 and base pair 834 in the degenerate sequence. This 279 base pair exon region is provided in FIG. 6 as SEQ ID NO:10. This exon sequence was blasted against a protein database (blastx) to confirm that the exon was RNA polymerase II and also against the translated database (tblastx) to insure that the exon was indeed an exon.

Since all plants and mammals possess RNA polymerase II, it was necessary to choose an exon that whose sequence shows low homology to any other organisms, besides maybe *C. elegans*. If an exon was chosen that demonstrated tight homology to other non-target organisms then RNA polymerase II may also be shut down in those organisms. When the above exon nucleotide sequence was blasted against other nucleotide sequence in the database (blastn), very little homology was demonstrated with any other organism besides *C. elegans*. From the various blast searches, it was decided that the antisense and sense fragments of the construct would be designed from this exon region.

The antisense-sense construct was cloned into the Bam HI and Kpn I sites of a pUC 119 based vector which possesses a 35S promoter and nos terminator regions necessary for gene expression in soybeans. Briefly, the primer pair RP2_KpnF1B/RP2_BamRB was designed to amplify a 273 bp antisense fragment from the exon region shown above.

The 285 bp fragment resulting from the amplification is provided in FIG. 7 as SEQ ID NO:13. The amplified fragment was cloned into pGEM-T-easy. The fragment was cut out of pGEM-T-easy using Kpn I and Bam HI enzymes and subsequently cloned behind the 35S promoter in the pUC119 based vector. The way the sequence is cloned into the vector is actually the reverse complement of the above sequence. The RP2_BamRB primer adds a BamHI site which is on the 5' end of the fragment once cloned into the vector. The RP2_KpnF1B primer adds a Kpn I site which is on the 3' end of the fragment once cloned into the vector. The sequence of the reverse complement is provided in FIG. 8 as SEQ ID NO:14. FIG. 9 provides a pictoral representation of the cloning strategy. Positive clones containing the antisense fragment were designated pRS1 KpnF1B-BamRB.

The sense fragment was then cloned into Kpn I and Sac I sites located behind the previously cloned antisense fragment. Briefly, a 243 bp sense fragment was amplified using the primer pair RP2$_{13}$ KpnF2B/RP2_SacRB. The forward primer RP2$_{13}$ KpnF2B is located 19 bp inside of the RP2_KpnF1B primer and the reverse primer RP2_SacRB is the same as the RP2_BamRB primer but adds a Sac I site instead of a Bam HI site.

```
                                                         (SEQ ID NO:15)
RP2_KpnF2B primer: TGAGGTACCGACGAAGACAGCGGACCATAC
30mer—The primer adds a Kpn I site to the sense
fragment (underlined)

(SEQ ID NO:16)
RP2_SacRB primer: TTCGAGCTCTCCAATGGTGTGTCCCTCGG
29mer—The primer adds a Sac I site to the sense
fragment (underlined)
```

Figure 11:
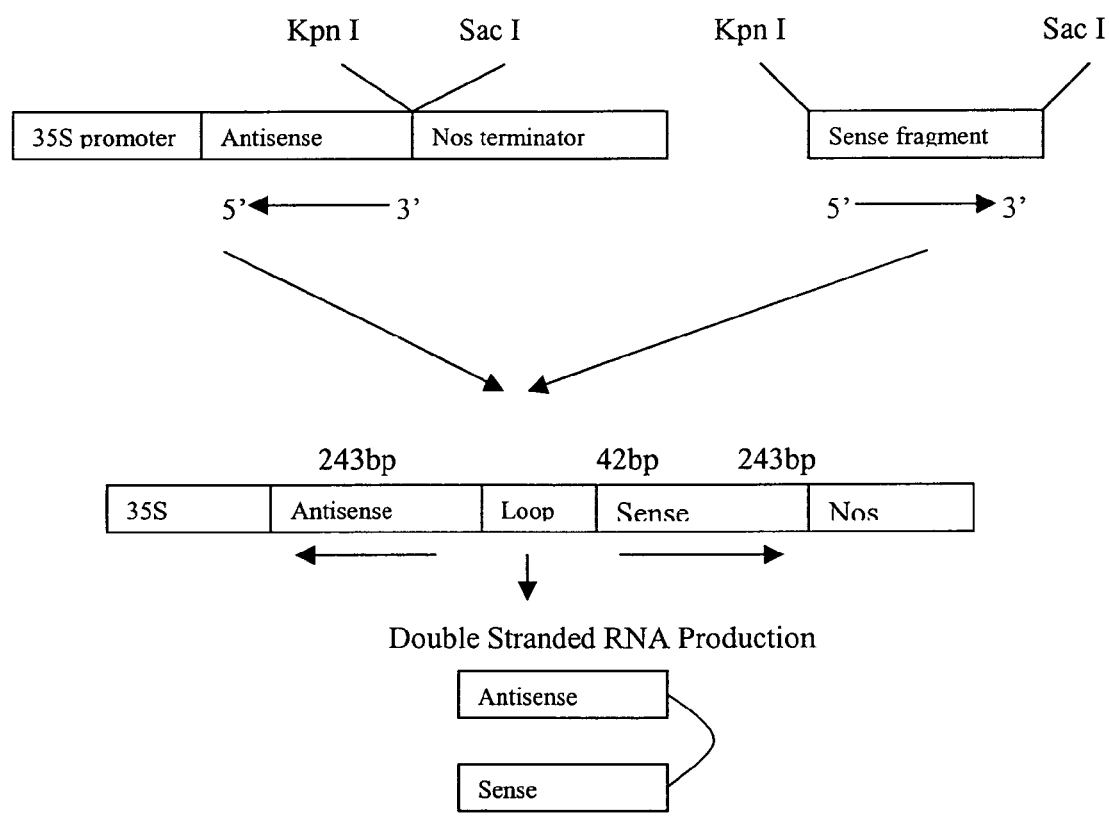
FIG. 11 provides a pictorial depiction of the cloning strategy for the RNA polymerase II RNAi construct.

The Kpn I and Sac I sites were added to sense fragment so that it could be cloned directly behind the antisense fragment. The sense fragment is provided in FIG. 10 as SEQ ID NO:17. The sequence amplified by these two primers is complementary to the sequence of the antisense fragment found in pRS1 KpnF1B-BamRB clone 14. The sequence in bold is sequence that is not complementary between the antisense and sense fragments. This non-complementary sequence is necessary so that the antisense and sense fragments are able to fold back onto one another and align during transcription, thus forming double strand RNA. The cloning strategy is depicted in FIG. 11.

Example 3

Chitin Synthase Constructs

This Example describes the construction of a chitin synthase RNAi gene. Chitin synthase gene was selected because in RNAi experiments by Piano et al. (Piano F, Schetter A J, Mangone M, Stein L D, Kemphues K J. RNAi analysis of genes expressed in the ovary of *Caenorhabditis elegans*. Current Biology 10: 1619) showed that silencing of this gene prevents development of nematode progeny (i.e. embryo lethal). The spliced sequenced together with Blockmaker (blocks.fhere.org), Codehop, and Clustalw to make degenerate primers and amplify the chitin synthase sequence from *Heterodera glycines*. This sequence is providing in FIG. 12 (SEQ ID NO: 18). Sense and antisense fragments are cloned from the underlined region using methods similar to those described above. The sense and antisense fragments are then cloned into vector as described in Example 2. Primers useful for cloning the sense and antisense sequences include the following:

| | | |
|---|---|---|
| CHSY151_F: | CCGATGCTTAGGCTGAC | (SEQ ID NO:19) |
| CHSY210_F: | CCAGCGGCAGTGATTC | (SEQ ID NO:20) |
| CHSY287_R: | AGCACACCTTCTCCAATC | (SEQ ID NO:21) |
| CHSY355_F: | TGGTACCAAAAGTTCGAGTAC | (SEQ ID NO:22) |
| CHSY409_F: | CATGTGTTCGGCTGTGT | (SEQ ID NO:23) |
| CHSY543_R: | ATCGGGTCTTCGCCTTG | (SEQ ID NO:24) |

Example 4

Reduction in the Number of Cysts in Transgenic Plants Expressing MSPi Gene

MSP is the major protein that required for nematode sperm motility. If this protein is disrupted, male sterility will result and female nematodes will not be fertilized and develop cysts. These examples describe experiments wherein soybean plants were genetically modified to express the MSPi construct described in Example 1. The results show a significant reduction in the amount of cysts from the transgenic plants as compared to the non-engineered controls.

Soybean somatic embryos were genetically modified using a particle gun to contain the pATMSPi construct (MSP RNAi), multiplied in tissue culture, and converted to plants. Several independent events from two cultivars were recovered containing this construction. The two cultivars were "Jack", a partially resistant cultivar, and "Chapman" a susceptible cultivar. Two bioassays were performed with these transgenic lines.

In the first bioassay the MSP RNAi transgenic plants were tested for SCN resistance. Events as well as non-engineered controls were transplanted into soil infected with soybean cyst nematodes (SCN) and grown in the greenhouse for six weeks. Soybean roots were then washed to remove soil and debris. SCN cysts were removed from each plant and the number of cysts, eggs per cysts and root weight data was collected for each replicate. Results are summarized in FIG. 13-18.

In the second bioassay, residual effects of the MSPi construction upon nematodes were evaluated. Cysts from replicates of each event and non-engineered checks were pooled independently and ground to release eggs. Eggs were then added to sterilized soil at a concentration of 1000 eggs/plant. "Flyer", a soybean variety with no resistance to SCN, was planted in this infected soil and grown for six weeks. At the end of the bioassay the roots were washed and data on cyst and egg production and root weight was recorded. Results are summarized in FIGS. 13-17.

Referring to FIG. 13, data from the first experiment shows a slight reduction in the number of cyst per plant when compared to the non-engineered control. In the second experiment even though the eggs harvested from the first experiment were applied to susceptible line (Flyer) at the rate, a 39.3% reduction in cysts was recorded from eggs harvested from the transgenic plants. Inference can be drawn from these results that 1) the MSPi construction does inhibit the cysts formation at a low level and 2) the effects of the transgene can be carried over to the next generation.

Referring to FIG. 14, data from the first experiment shows a 49.4% reduction in the number of cyst per gram of root when compared to the non-engineered control. In the second experiment a difference (34.0% reduction) was recorded. Inference can be drawn from these results that 1) the MSPi construction does inhibit the cysts formation at some level and 2) the effects of the transgene can be carried over to the next generation.

Referring to FIG. 15, data from the first experiment shows a 35.5% reduction in the number of SCN eggs per plant when compared to the non-engineered control. In the second experiment even though the eggs of the first experiment were applied to susceptible line (Flyer) at the same rate (1000 eggs per plant) a significant difference (29.0% reduction) was recorded in the eggs from the transgenic plants. SCN eggs used for inoculation in Experiment 2 originated from eggs collected in Experiment 1. SCN eggs from transgenic lines were applied at the same rate. Inference can be drawn from these results that 1) the MSPi construction does inhibit the egg production at some level and 2) the effects of the transgene was carried over to the next generation of SCN.

Referring to FIG. 16, data from the first experiment shows a 32.5% reduction in the number of SCN eggs per gram root when compared to the non-engineered control. In the second experiment even though the eggs of the first experiment were applied to susceptible line (Flyer) a significant difference (25.1% reduction) was recorded. SCN eggs used for inoculation in Experiment 2 originated from eggs collected in Experiment 1. SCN eggs from transgenic lines were applied at the same rate. Inference can be drawn from these results that 1) the MSPi construction does inhibit the egg production at some level and 2) the effects of the transgene was carried over to the next generation of SCN.

Referring to FIG. 17, data from the first experiment shows a small reduction in the number of SCN eggs per cyst when compared to the non-engineered control. This reduction was not significant when the data was statistically analyzed. This trend continued in the second experiment. Inference can be drawn from these results that 1) the MSPi construction effect the number of eggs per cyst when cyst develop and 2) the effects of the transgene on eggs/cysts do not carry over to the next generation of SCN.

In summary, the results show that soybean plants transformed with the MSP RNAi construction do have significant levels of resistance to soybean cyst nematode. In addition, SCN progeny obtained from roots of these plants have a reduced ability to infect susceptible cultivars suggesting retention of the phenotype. Transgenic plants containing the MSP RNAi construction presumably cause a significant amount of males to become sterile thereby reducing the amount of cysts. It also appears the effect of the RNAi molecules can be seen in the progeny of SCN feeding on the nontransgenic plants.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, plant biology, biochemistry, or related fields are intended to be within the scope of the following claims.

We claim:

1. A transgenic plant comprising a nucleic acid sequence having a sense sequence linked to its complementary antisense sequence and encoding a double stranded RNA that inhibits expression of a *Heterodera glycines* embryonic lethal phenotype gene, wherein the sense or antisense sequence comprises SEQ ID NO: 1, SEQ ID NO: 9 or SEQ ID NO: 18, wherein nematodes ingesting said double stranded nematode RNA do not proliferate, and wherein said transgenic plant exhibits increased resistance to soybean cyst nematodes as compared to a control plant.

2. Seed from the transgenic plant of claim 1, wherein said seed comprise said nucleic acid sequence.

3. A vector comprising a nucleic acid sequence having a sense sequence linked to its complementary anstisense and encoding a double stranded RNA sequence that inhibits expression of a *Heterodera glycines* embryonic lethal phenotype gene, wherein said sense sequence or antisense sequence comprises SEQ ID NO: 1, SEQ ID NO: 9 or SEQ ID NO: 18; and wherein nematodes ingesting said double stranded nematode RNA do not proliferate.

4. The vector of claim 3, wherein said nucleic acid sequence comprises a sense sequence linked to its complementary antisense sequence, said nucleic acid sequence being operably linked to a plant promoter.

5. The vector of claim 3, wherein said nucleic acid sequence comprises a sense sequence and its complementary antisense sequence separated by a loop sequence.

6. The vector of claim 4, wherein said promoter is a tissue specific promoter.

7. The vector of claim 4, wherein said promoter is a constitutive promoter.

8. The vector of claim 3, wherein said nucleic acid sequence comprises a sense sequence and its complementary antisense sequence each operably linked to separate promoters.

9. A transgenic soybean plant comprising the vector of claim 3; said transgenic soybean plant exhibits increased resistance to soybean cyst nematodes as compared to a control plant.

10. A method for controlling *Heterodera glycines* comprising providing a transgenic soybean plant comprising a nucleic acid sequence having a sense sequence linked to its complementary anstisense and encoding a double stranded RNA that inhibits expression of a *Heterodera glycines* embryonic lethal phenotype gene, wherein the proliferation of nematodes feeding on said plant is reduced as compared to nematodes feeding on non-transgenic plant and wherein said sense sequence or antisense sequence comprises SEQ ID NO: 1, SEQ ID NO:9 and SEQ ID NO:18.

11. The method of claim 10, wherein said nucleic acid sequence is on a vector.

12. The method of claim 11, wherein said nucleic acid sequence comprises a sense sequence and its complementary antisense sequence operably linked to a plant promoter.

13. The method of claim 12, wherein said sense sequence and said antisense sequence are operably linked to the same promoter.

14. The method of claim 12, wherein said promoter is a tissue specific promoter.

15. The method of claim 12, wherein said promoter is a constitutive promoter.

16. The method of claim 10, wherein said sense sequence and said antisense sequence are separated by a loop sequence.

17. A transgenic plant comprising a nucleic acid encoding a double stranded RNA that causes decreased proliferation of soybean cyst nematodes feeding on said transgenic plant as compared to soybean cyst nematodes feeding on non-transgenic plants, wherein one strand of said double stranded RNA is complementary to a nematode embryonic lethal phenotype gene, and wherein said one strand comprises a sequence selected from the group consisting of SEQ ID NO: 1, SEQ ID NO: 9 and SEQ ID NO: 18.

* * * * *